Figure 1A:
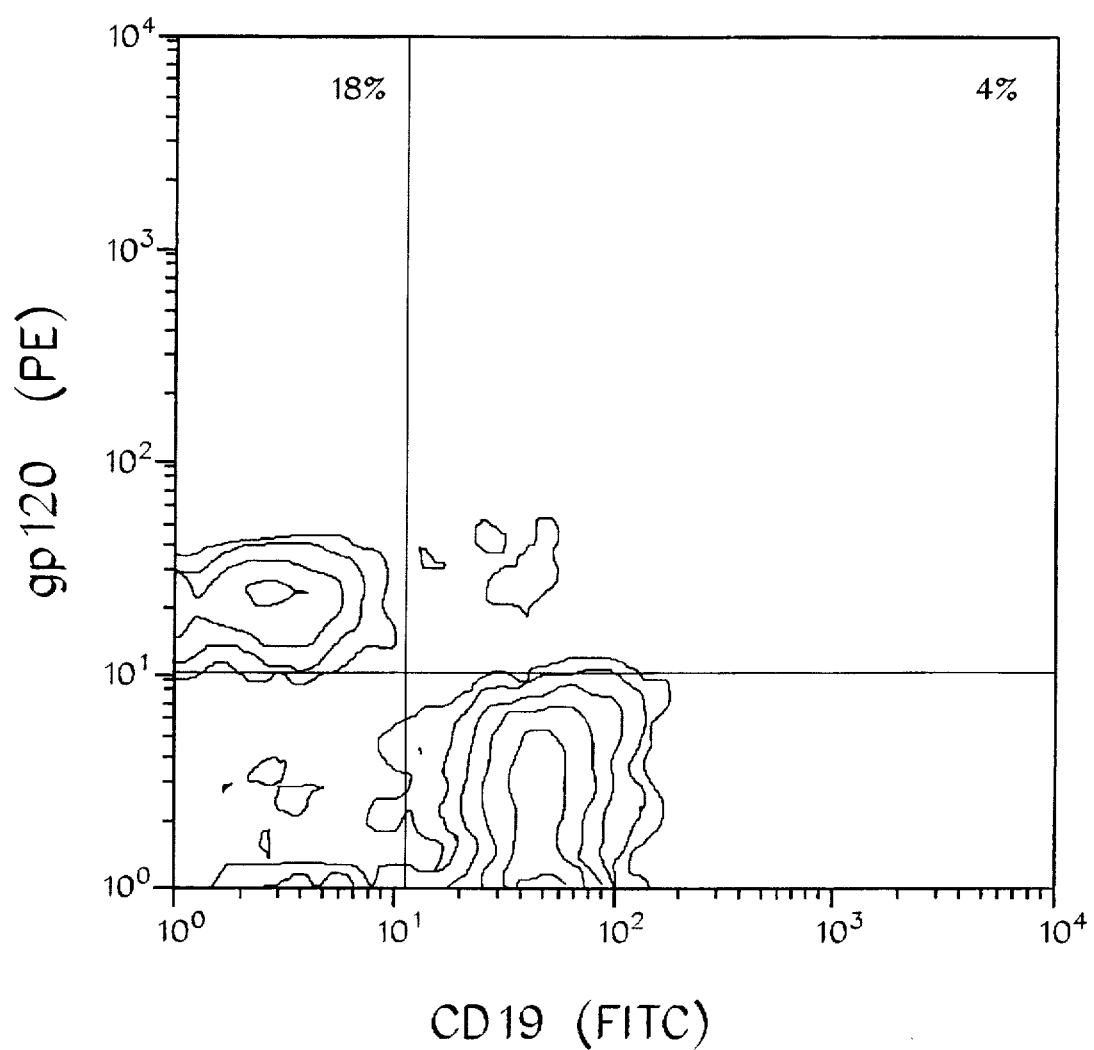

United States Patent [19]

Braun et al.

[11] Patent Number: 5,691,135
[45] Date of Patent: Nov. 25, 1997

[54] IMMUNOGLOBULIN SUPERANTIGEN BINDING TO GP 120 FROM HIV

[75] Inventors: Jonathan Braun, Sherman Oaks; Lee A. Goodglick, Los Angeles, both of Calif.

[73] Assignee: The Regents of the University of California, Oakland, Calif.

[21] Appl. No.: 306,116

[22] Filed: Sep. 14, 1994

Related U.S. Application Data

[63] Continuation-in-part of Ser. No. 259,669, Jun. 14, 1994, abandoned, which is a continuation of Ser. No. 9,705, Jan. 26, 1993, abandoned.

[51] Int. Cl.$^6$ ..................................................... C12Q 1/70
[52] U.S. Cl. .................. 435/5; 435/7.1; 435/7.2; 435/7.24; 435/7.92; 435/974
[58] Field of Search .................................. 435/5, 7.1, 7.2, 435/7.24, 7.92, 974

[56] References Cited

PUBLICATIONS

Goodglick et al, "Mapping the Ig Superantigen–Binding Site of HIV–1 gp120" *Journal of Immunology*, vol. 155, No. 11 (1995), pp. 5151–5159.

Berberian et al, "Immunoglobulin VH3 Gene Products: Natural Ligands for HIV gp120", *Science*, vol. 261, No. 5128 (1993), pp. 1588–1591.

*Primary Examiner*—Christine M. Nucker
*Assistant Examiner*—Jeffrey Stucker
*Attorney, Agent, or Firm*—Knobbe Martens Olson & Bear, LLP

[57] ABSTRACT

VH3 and VH4 type immunoglobulins display superantigen-type binding affinity for the HIV gp120 envelope glycoprotein. VH3 and VH4 type antibody molecules, including IgG and IgM, are shown to suppress HIV infection in vivo and in vitro. Determining the level of such antibody molecules is correlated to the advancement of HIV disease state.

3 Claims, 23 Drawing Sheets

COMPARISON OF PEPTIDES: INHIBITION OF HEA BINDING TO gp120

| PEPTIDE # | gp120 DOMAIN | AMINO ACID | INHIBITION OF HEA BINDING | SEQUENCE |
|---|---|---|---|---|
| 1590 | V3 | 295-321 | – | TRPNNNTRKSIRIQRGPGRAFVITGKIGNMRQAH (SEQ ID NO. 14) |
| 1985 | V3 | 301-320 | – | CTRPNYNKRKRIHIGPGRAF (SEQ ID NO. 15) |
| 864 | V3 | 306-327 | – | YNKRKRIHIQRGPGRAFYTTKNII (SEQ ID NO. 16) |
| 1987 | V3-C3 | 321-340 | – | YTTKNIIGTRQAHCNISRA (SEQ ID NO. 17) |
| 1988 | C3 | 331-350 | + | RQAHCNISRAKWNDTLROIV (SEQ ID NO. 18) |
| 1989 | C3 | 341-360 | + | KWNDTLROIVSKLKEQFKNK (SEQ ID NO. 19) |
| 1990 | C3 | 351-370 | – | SKLKEQFKNKTIVFNQSSGG (SEQ ID NO. 21) |
| 1587 | C3 | 350-378 | – | REQFGNNKTIIFKQSSGGDPEIVTHSFNC (SEQ ID NO. 20) |
| | | | | |
| 703 | C4 | 419-438 | – | TGDIITLPCRIKQIINRWQV (SEQ ID NO. 25) |
| 1589 | C4 | 418-441 | + | CRIKOIINMWOKVGKAMYAPPISG (SEQ ID NO.C 24) |
| 2007 | C4 | 421-440 | + | KOIINMWOEVGKAMYAPPIE (SEQ ID NO. 23) |
| 2008 | C4 | 431-450 | – | GKAMYAPPIEGQIRCSSNIT (SEQ ID NO. 26) |
| | | | | |
| 747 | C2 | 200-217 | – | VITQACPKVSFEPIPIHY (SEQ ID NO. 7) |
| 748 | C2 | 210-227 | – | FEPIPIHYCAPAGFAILK (SEQ ID NO. 8) |
| 749 | C2 | 223-238 | – | CAPAGFAILKCNDKKF (SEQ ID NO. 9) |
| 1959 | C2 | 231-250 | + | LKCNDKKFSGKGSCKNVSTV (SEQ ID NO. 11) |
| 1960 | C2 | 241-260 | + | KSGCKNVSTVQCTHGIRPVV (SEQ ID NO. 12) |
| 743 | C2 | 228-246 | – | CNNKTFNGTGPCTNVSTVQ (SEQ ID NO. 10) |
| 746 | C2 | 236-254 | – | TGPCTNVSTVQCTHGIRPV (SEQ ID NO. 13) |

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:1:

Met Arg Val Lys Gly Ile Arg Arg Asn Tyr Gln His Trp Trp Gly Trp
1               5                   10                  15
Gly Thr Met ( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Glu Lys Leu Trp Val Thr Val Tyr Tyr Gly Val Pro Val Trp Lys Glu
 1               5                   10                  15

Ala Thr Thr Thr
            20
```

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:3:

```
Val Pro Val Trp Lys Glu Ala Thr Thr Thr Leu Phe Cys Ala Ser Asp
 1               5                   10                  15

Ala Lys Ala Tyr
            20
```

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:4:

```
Glu Gln Met His Glu Asp Ile Ile Ser Leu Trp Asp Gln Ser Leu Lys
 1               5                   10                  15

Pro Cys Val Lys
            20
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:5:

Asp Thr Glu Val His Asn Val Trp Ala Thr Gln Ala Cys Val Pro Thr
1               5                   10                  15

Asp Pro Asn Pro
            20

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:6:

Glu Gly Thr Ile Lys Gly Gly Glu Met Lys Asn Cys Ser Phe Asn Ile
1               5                   10                  15

Thr Thr Ser Ile
            20

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:7:

Val Ile Thr Gln Ala Cys Pro Lys Val Ser Phe Glu Pro Ile Pro Ile
1               5                   10                  15

His Tyr ( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:8:

Phe Glu Pro Ile Pro Ile His Tyr Cys Ala Pro Ala Gly Phe Ala Ile
1               5                   10                  15
Leu Lys (2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:9:

Cys Ala Pro Ala Gly Phe Ala Ile Leu Lys Cys Asn Asp Lys Lys Phe
1               5                   10                  15

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:10:

Cys Asn Asn Lys Thr Phe Asn Gly Thr Gly Pro Cys Thr Asn Val Ser
1               5                   10                  15
Thr Val Gln (2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:11:

Leu Lys Cys Asn Asp Lys Lys Phe Ser Gly Lys Gly Ser Cys Lys Asn
1               5                   10                  15

```
Val Ser Thr Val
            20
```

(2) INFORMATION FOR SEQ ID NO:12:

(i) SEQUENCE CHARACTERISTICS:
  (A) LENGTH: 20 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:12:

```
Lys Gly Ser Cys Lys Asn Val Ser Thr Val Gln Cys Thr His Gly Ile
 1           5                   10                  15
Arg Pro Val Val
            20
```

(2) INFORMATION FOR SEQ ID NO:13:

(i) SEQUENCE CHARACTERISTICS:
  (A) LENGTH: 19 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:13:

```
Thr Gly Pro Cys Thr Asn Val Ser Thr Val Gln Cys Thr His Gly Ile
 1           5                   10                  15
Arg Pro Val
```

(2) INFORMATION FOR SEQ ID NO:14:

(i) SEQUENCE CHARACTERISTICS:
  (A) LENGTH: 34 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:14:

```
Thr Arg Pro Asn Asn Asn Thr Arg Lys Ser Ile Arg Ile Gln Arg Gly
 1           5                   10                  15
```

```
Pro Gly Arg Ala Phe Val Ile Thr Gly Lys Ile Gly Asn Met Arg Gln
         20                  25                  30
Ala His
```

( 2 ) INFORMATION FOR SEQ ID NO:15:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:15:

```
Cys Thr Arg Pro Asn Tyr Asn Lys Arg Lys Arg Ile His Ile Gly Pro
 1               5                  10                  15
Gly Arg Ala Phe
         20
```

( 2 ) INFORMATION FOR SEQ ID NO:16:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:16:

```
Tyr Asn Lys Arg Lys Arg Ile His Ile Gln Arg Gly Pro Gly Arg Ala
 1               5                  10                  15
Phe Tyr Thr Thr Lys Asn Ile Ile
         20
```

( 2 ) INFORMATION FOR SEQ ID NO:17:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:17:

Tyr Thr Thr Lys Asn Ile Ile Gly Thr Ile Arg Gln Ala His Cys Asn
1               5                   10                  15

Ile Ser Arg Ala
            20

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:18:

Arg Gln Ala His Cys Asn Ile Ser Arg Ala Lys Trp Asn Asp Thr Leu
1               5                   10                  15

Arg Gln Ile Val
            20

( 2 ) INFORMATION FOR SEQ ID NO:19:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:19:

Lys Trp Asn Asp Thr Leu Arg Gln Ile Val Ser Lys Leu Lys Glu Gln
1               5                   10                  15

Phe Lys Asn Lys
            20

( 2 ) INFORMATION FOR SEQ ID NO:20:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:20:

5,691,135

45

-continued

Arg Glu Gln Phe Gly Asn Asn Lys Thr Ile Ile Phe Lys Gln Ser Ser
 1               5                  10                  15
Gly Gly Asp Pro Glu Ile Val Thr His Ser Phe Asn Cys
                20                  25

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:21:

Ser Lys Leu Lys Glu Gln Phe Lys Asn Lys Thr Ile Val Phe Asn Gln
 1               5                  10                  15
Ser Ser Gly Gly
                20

( 2 ) INFORMATION FOR SEQ ID NO:22:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:22:

Thr Gly Asn Ile Thr Leu Pro Cys Arg Ile Lys Gln Val Val Arg Thr
 1               5                  10                  15
Trp Gln Gly ( 2 ) INFORMATION FOR SEQ ID NO:23:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:23:

Lys Gln Ile Ile Asn Met Trp Gln Glu Val Gly Lys Ala Met Tyr Ala
1               5                   10                  15

Pro Pro Ile Glu
            20

( 2 ) INFORMATION FOR SEQ ID NO:24:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:24:

Cys Arg Ile Lys Gln Ile Ile Met Trp Gln Lys Val Gly Lys Ala Met
1               5                   10                  15

Tyr Ala Pro Pro Ile Ser Gly
            20

( 2 ) INFORMATION FOR SEQ ID NO:25:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:25:

Thr Gly Asp Ile Ile Thr Leu Pro Cys Arg Ile Lys Gln Ile Ile Asn
1               5                   10                  15

Arg Trp Gln Val
            20

( 2 ) INFORMATION FOR SEQ ID NO:26:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:26:

Gly Lys Ala Met Tyr Ala Pro Pro Ile Glu Gly Gln Ile Arg Cys Ser
1               5                   10                  15

Ser Asn Ile Thr
            20

( 2 ) INFORMATION FOR SEQ ID NO:27:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:27:

Arg Pro Gly Gly Gly Asp Met Arg Asp Asn Trp Arg Ser Glu Leu Tyr
1               5                   10                  15

Lys Tyr Lys Val
            20

( 2 ) INFORMATION FOR SEQ ID NO:28:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:28:

Trp Arg Ser Glu Leu Tyr Lys Tyr Lys Val Val Thr Ile Glu Pro Leu
1               5                   10                  15

Gly Val Ala Pro
            20

( 2 ) INFORMATION FOR SEQ ID NO:29:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:29:

Thr Lys Ala Lys Arg Arg Val Val Gln Arg Glu Lys Arg Ala Ala Ile
1               5                   10                  15

Gly Ala Leu Pro
            20

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:30:

Glu Ala Gln Gln His Met Leu Gln Leu Thr Val Trp Gly Ile Lys Gln
1               5                   10                  15

Leu Gln Ala Arg
            20

( 2 ) INFORMATION FOR SEQ ID NO:31:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:31:

Val Trp Gly Ile Leu Gln Leu Gln Ala Arg Val Leu Ala Val Glu Arg
1               5                   10                  15

Tyr Leu Lys Asp
            20

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:32:

Lys Gly Ser Cys Lys Asn Val Ser Thr Val
 1               5                   10

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:33:

Lys Gly Ile Arg Arg Asn Tyr Gln His Trp
 1               5                   10

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:34:

Lys Gln Ile Ile Asn Met Trp Gln Glu Val
 1               5                   10

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:35:

Lys Gln Ile Ile Asn Met Trp Gln Lys Val
 1               5                   10

( 2 ) INFORMATION FOR SEQ ID NO:36:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:36:

```
Lys Trp Asn Asp Thr Leu Arg Gln Ile Val
 1               5                    10
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:37:

```
Lys Gln Ile Ile Asn Arg Trp Gln Val
 1               5
```

( 2 ) INFORMATION FOR SEQ ID NO:38:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:38:

```
Lys Asn Ile Ile Gly Thr Arg Gln Ala His
 1               5                    10
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:39:

```
Thr Gly Pro Cys Thr Asn Val Ser Thr Val
 1               5                  10
```

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:40:

```
Lys Asn Ile Ile Gly Thr Ile Arg Gln Ala
 1               5                  10
```

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:41:

```
Lys Ala Met Tyr Ala Pro Pro Ile Glu Gly
 1               5                  10
```

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal -continued ( v i ) ORIGINAL SOURCE:

( x i ) SEQUENCE DESCRIPTION: SEQ ID NO:42:

Lys Glu Ala Thr Thr Thr Leu Phe Cys Ala
1               5                       10

( 2 ) INFORMATION FOR SEQ ID NO:43:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( i x ) FEATURE:
        ( A ) NAME/KEY: Other
        ( B ) LOCATION: 2..2
        ( D ) OTHER INFORMATION: Position 2 is nonpolar
        ( A ) NAME/KEY: Other
        ( B ) LOCATION: 3..3
        ( D ) OTHER INFORMATION: Position 3 is Ile or Ser
        ( A ) NAME/KEY: Other
        ( B ) LOCATION: 5..6
        ( D ) OTHER INFORMATION: Position 5 is polar, Position
            6 is aliphatic nonpolar ( x i ) SEQUENCE DESCRIPTION: SEQ ID NO:43:

Lys Xaa Xaa Xaa Xaa Xaa Xaa Gln Xaa Val
1               5                       10

IMMUNOGLOBULIN SUPERANTIGEN BINDING TO GP 120 FROM HIV

RELATED APPLICATIONS

This application is a continuation-in-part of U.S. application Ser. No. 08/259,669, filed Jun. 14, 1994, now abandoned, which is a continuation of U.S. application Ser. No. 08/009,705, filed Jan. 26, 1993 now abandoned. The disclosures of these related applications are hereby incorporated herein by this reference thereto.

GOVERNMENT INTEREST IN THE INVENTION

Certain aspects of the invention disclosed herein were made with United States government support under grant number CA 12800 from the National Institutes of Health. Accordingly, the United States Government has certain rights in the invention.

FIELD OF THE INVENTION

The present invention relates generally to the field of vaccines. More specifically, the invention relates to the inhibition of HIV infection by stimulating VH3 and VH4 antibody responses.

BACKGROUND OF THE INVENTION

A variety of natural and synthetic compounds have recently drawn attention because they function as superantigens. Superantigens are defined by their capacity to associate with the framework regions of V gene products, and hence an unusually high fraction of antigen-receptor complexes. Curiously, the scientific literature in this field deals almost exclusively with superantigens that bind T-lymphocyte antigen receptors. Only a few examples of superantigens that bind immunoglobulins (Ig's) have been disclosed.

Figure 5A:
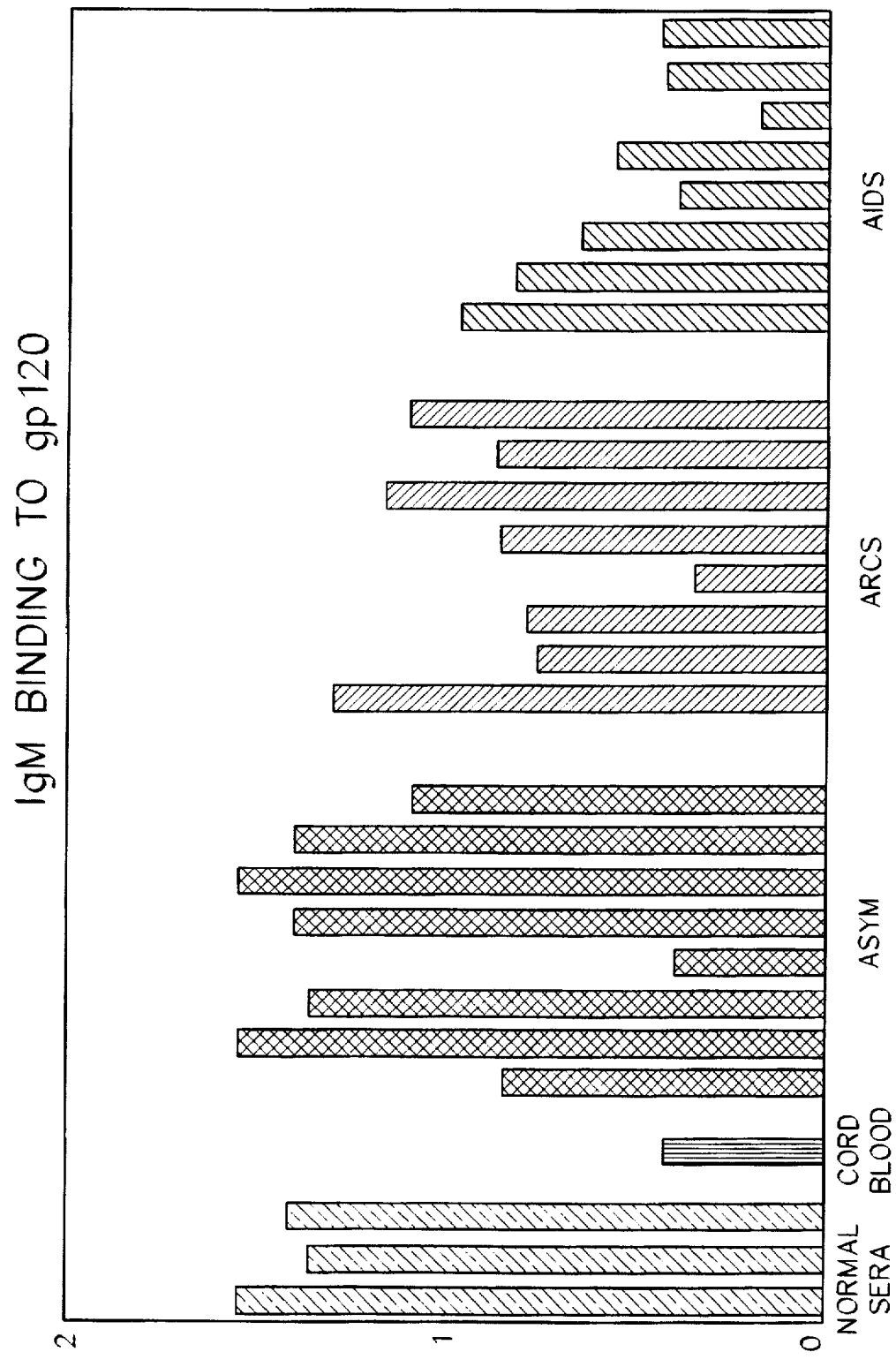
Figure 5B:
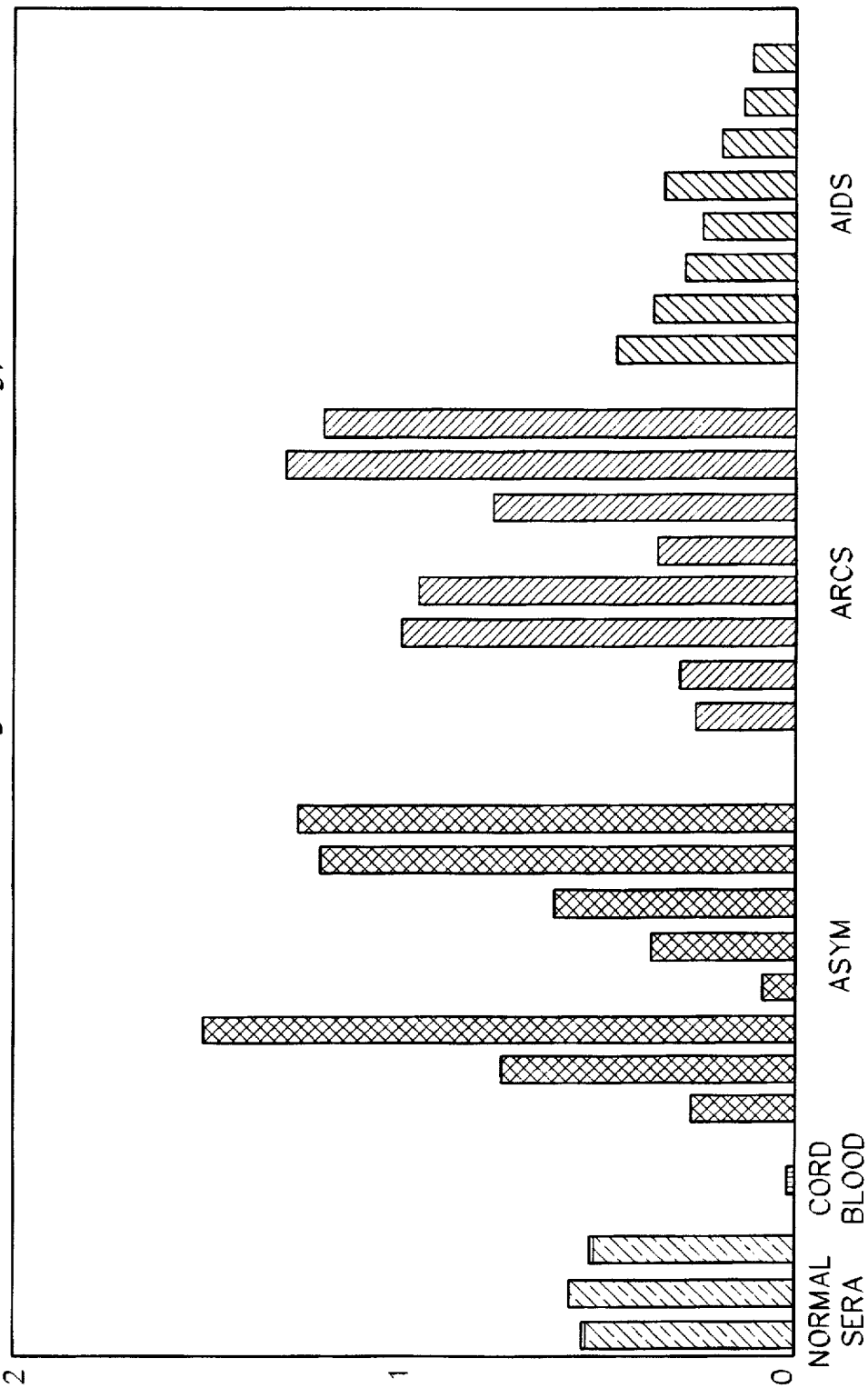

Protein A of *Staphylococcus aureus* is one example of a superantigen that binds immunoglobulins. In fact, Protein A binds to the variable region domain of a high percentage of immunoglobulins derived from the VH3 gene family. Immunoglobulin superantigens are natural or synthetic compounds that associate with the immunoglobulins by virtue of a specific avidity for Ig variable regions. These immunoglobulin variable regions can be any conventional or surrogate V, D, or J gene segment of the light or heavy chain class.

It was recently discovered that patients infected with the human immunodeficiency virus (HIV) were deficient in Bocells expressing VH3 genes (Berberian et al., Blood 78:175–179 (1991)). VH3 is the largest Ig heavy chain variable region family. Indeed, the VH3 family consists of 30 or more related gene segments.

Acquired immunodeficiency syndrome (AIDS) is characterized by dysfunction and depletion of immune cells, including CD4 T-cells and B-cells. CD4 T-cells are selectively depleted by a chain of events that initiates with the binding of the human immunodeficiency virus (HIV) to the CD4 molecule via the gp120 viral envelope glycoprotein. The mechanism by which virus binding ultimately leads to depletion of this cellular population is unknown. Models invoking direct cytotoxicity, gp120-induced polyclonal apoptosis, and oligoclonal superantigen-mediated deletion have been proposed to explain this phenomenon. The mechanism by which HIV binds to B cells is also unknown.

Prompted by this finding, the research program of the inventor initially led to the unanticipated conclusion, that HIV gp120 is an Ig superantigen. Some of these findings were reported after the parent application was filed (Berberian et al., in *Science* 261:1588 (1993)). These and other descriptive information are listed in the following set of figures.

BRIEF DESCRIPTION OF THE FIGURES

FIGS. 1A–D show the graphic results of fluorescence activated cell sorting procedures used to detect the interaction between HIV gp120 and a subpopulation of B cells. (A) Detection of a minor population of $CD19^+$ gp120-binding cells using flow cytometry. Mononuclear human tonsil cells were sequentially stained with HIV-$1_{SF2}$ gp120, goat anti-gp120, swine anti-goat IgG-PE, and anti-CD19-FITC. 4% of B-cells ($CD19^+$) and 68% of T-cells ($CD19^-$) bound gp120. Staining with anti-CD20 and anti-CD3 confirmed the identity of these cell types ($CD20^{+/CD}3^-$ and $CD20^-/CD3^-$, respectively; data not shown).

(B) Effect of anti-CD4 pretreatment on gp120-binding. Tonsil cells were pretreated with the anti-CD4 antibody Leu3a (40 ng, 30 minutes at 4° C.), washed, then stained as in (A). Leu3a pretreatment inhibited T-cell binding to gp120 (upper left quadrant) but did not affect B-cell binding to gp 120 (upper right quadrant).

(C), (D) Effect of membrane Ig endocytosis on gp120-binding. Tonsil cells were pretreated with anti-human K and λ light chain to elicit membrane Ig endocytosis, then washed and stained for CD19 and either membrane IgD (C) or gp120-binding (D). Values are the mean fluorescence calculated from flow cytometric data on gaited $CD19^+$ cells. Background staining was determined with fluorochrome-labelled isotype control antibodies. Note the similar decrease in membrane Ig and gp120-binding in anti-Ig treated cells.

FIGS. 2A–B show histograms illustrating gp120-binding by FACS sorted Epstein Barr virus-transformed B-cells. EBV-transformed mantle zone tonsil cells were FACS-sorted into gp120-binding and gp120-nonbinding populations, then reanalyzed after expansion in culture for three weeks. Fluorescence histograms for gp120-binding (solid line) or background staining with all reagents except gp120 (dotted line). (A) Sorted gp $120^-$ cells; (B) sorted $gp120^+$ cells. Note the persistence of the original sorted gp120-binding phenotypes.

FIGS. 3A–C show graphic results of ELISA procedures to detect binding of immunoglobulin to gp120 in a cell-free system. Binding of Ig to HIV-$1_{SF2}$ rgp120 was measured by ELISA. (A) Normal serum assayed with anti-IgM (○) or anti-IgG (●). (B) IgG-depleted normal serum Ig separated into fractions enriched (■) or depleted (□) for protein A-binding (19; see Table 2).(C) Monoclonal IgM paraproteins to gp120. A0103 (■); HEA (□); RJ293 (○); SMI (●); normal serum (▲). In all figures, values are the mean of triplicate determinations, and error bars indicate standard deviations.

FIGS. 4A–B show the graphic results of procedures used to demonstrate that VH3 antibodied neutralized HIV-1 infection of target cells. All manipulations were in serum-free medium (AIM V, Bethesda Research Laboratory). (A) Monoclonal antibodies SMI (□) and A0103 (♦) were incubated with HIV-1 prior to culture on IL-2 stimulated peripheral blood lymphocytes (PBLs). A0103 binds gp120, whereas SMI does not bind gp120. (B) VH3 IgM purified from serum by sequential affinity chromatography (using protein G depletion and protein A enrichment) was incubated with HIV-1 prior to culture on IL-2 stimulated PBLs. The results are representative of three experiments.

FIGS. 5A–B show graphic results of an ELISA procedure to detect gp120-binding serum antibodies. Sera from 34 individuals with different clinical stages of HIV infection were measured by ELISA for (A) anti-gp120 IgM and (B) total serum VH3 (B6 idiotype). OD values for each group and parameter were compared as indicated using student's t-test.

Figure 6:
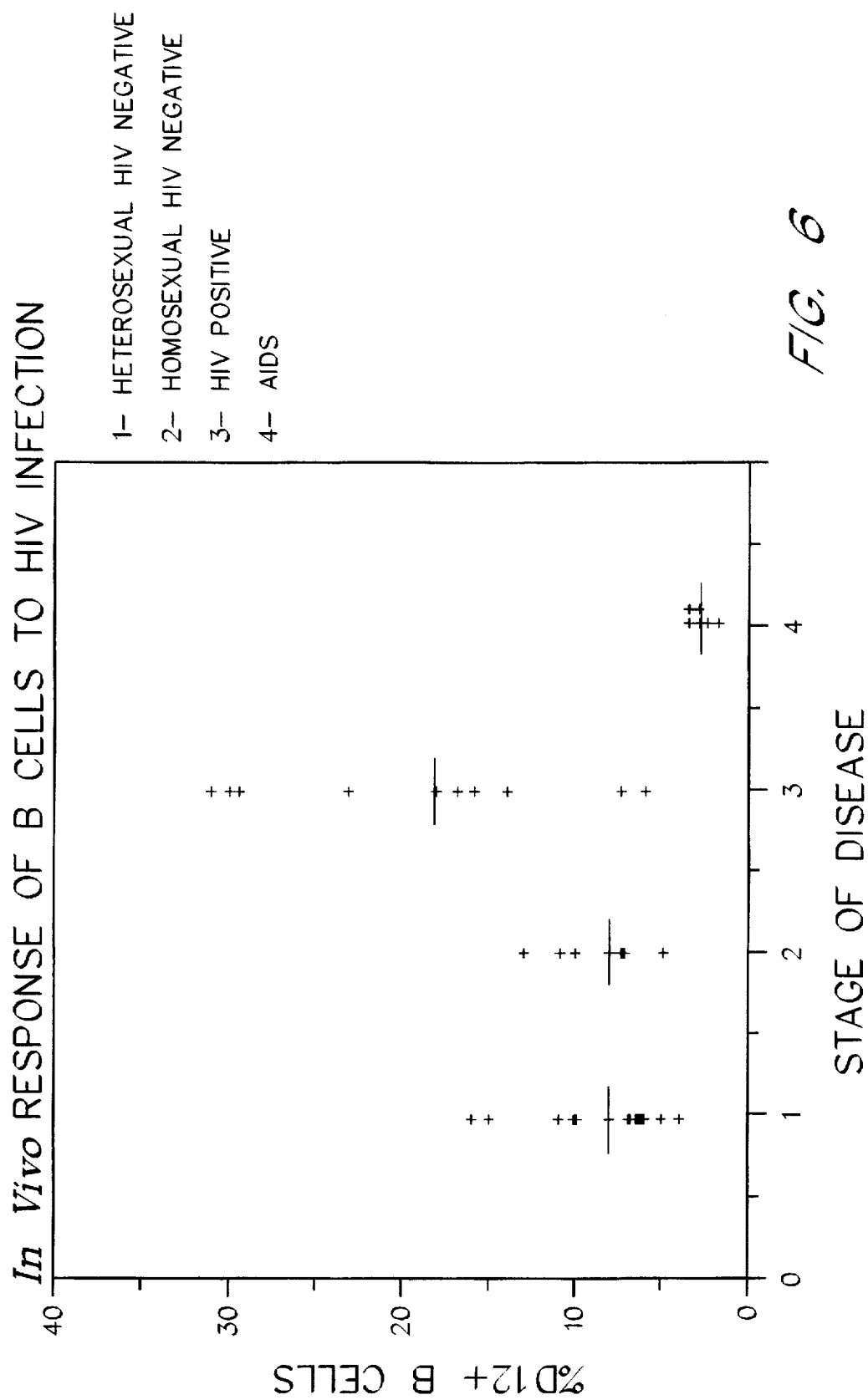

FIG. 6. Plot of in vivo response of B cells to HIV infection. The vertical axis represents the percentage of VH3 B cells in the total B cell population of the patient. The horizontal axis is divided into the disease stage of each patient group. Group 1 is HIV negative (heterosexual), Group 2 is HIV negative (homosexual), Group 3 is HIV positive, and Group 4 is AIDS positive.

Figure 7:
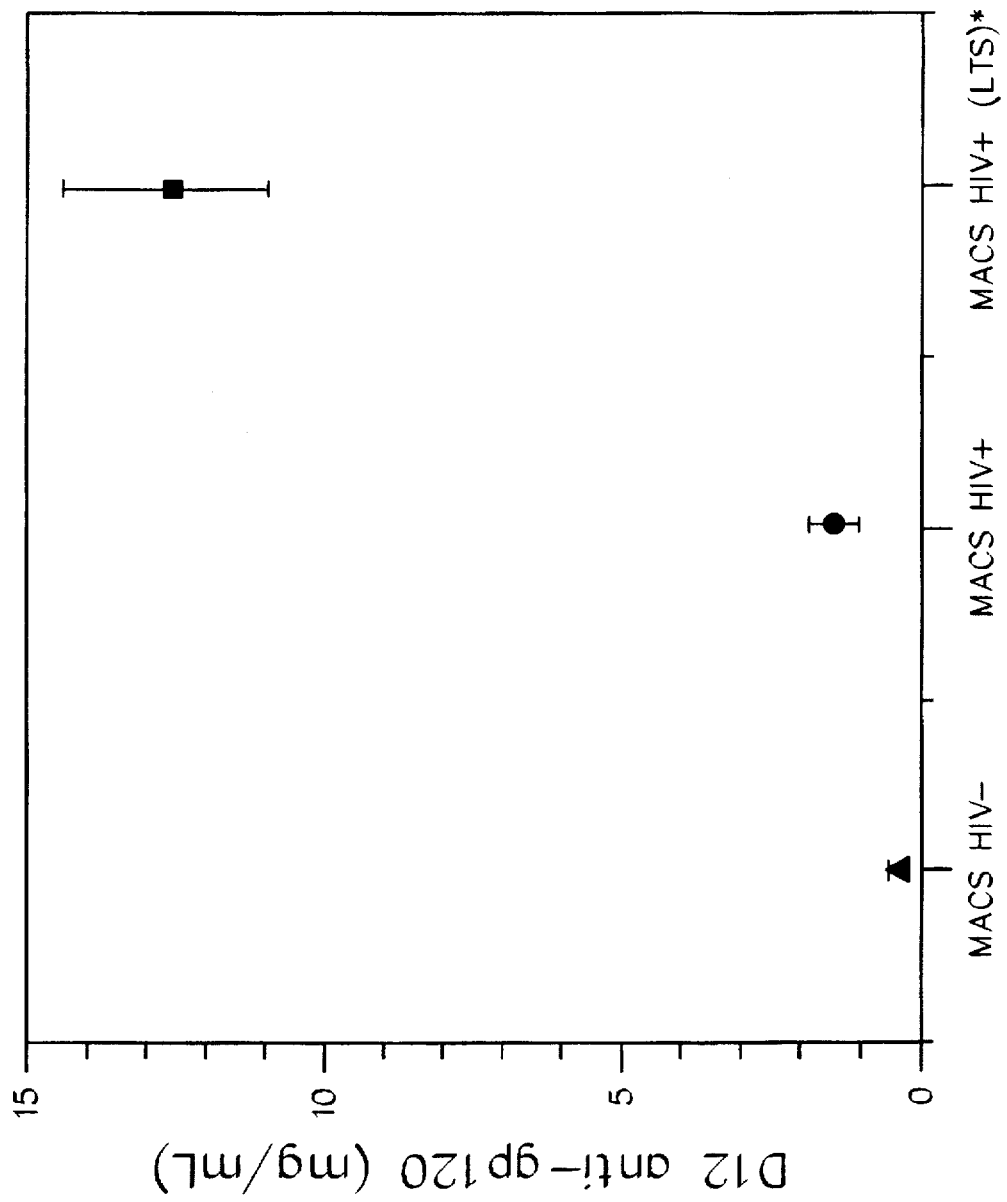

FIG. 7. Scatter plot of D12 anti-gp 120 IgM for three groups of individuals The concentrations of D12 anti-gp120 IgM were determined for serum samples isolated from HIV seronegative (HIV−), HIV seropositive (HIV+), and HIV seropositive long term survivors (LTS).

Figure 8:
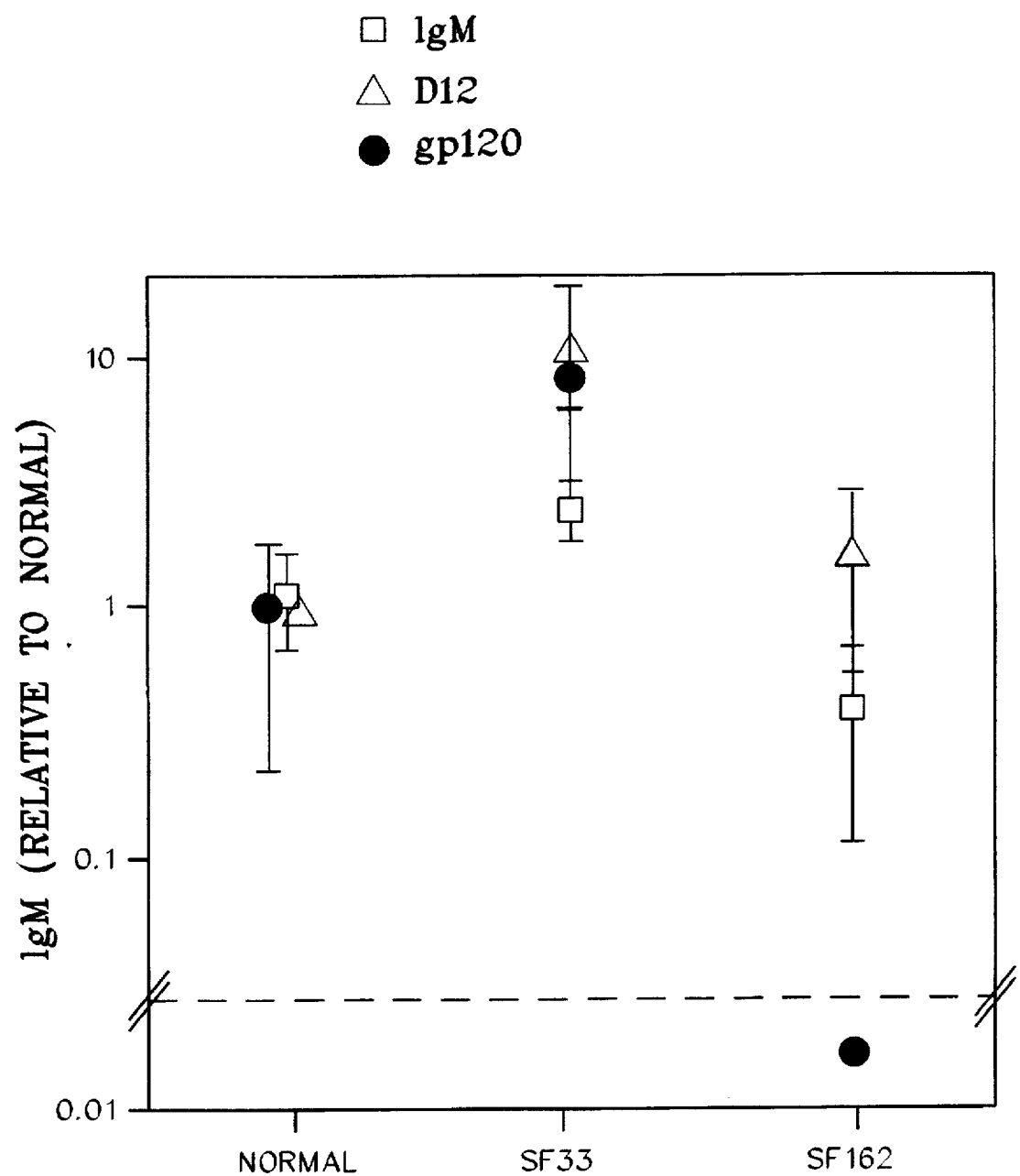

FIG. 8. Scatter plot of IgM levels in serum of SCID-hu mice infected with two strains of HIV-1. The plot shows relative levels of total IgM, D12 IgM, and anti-gp120 IgM compared to normal controls (uninfected).

Figure 9A:
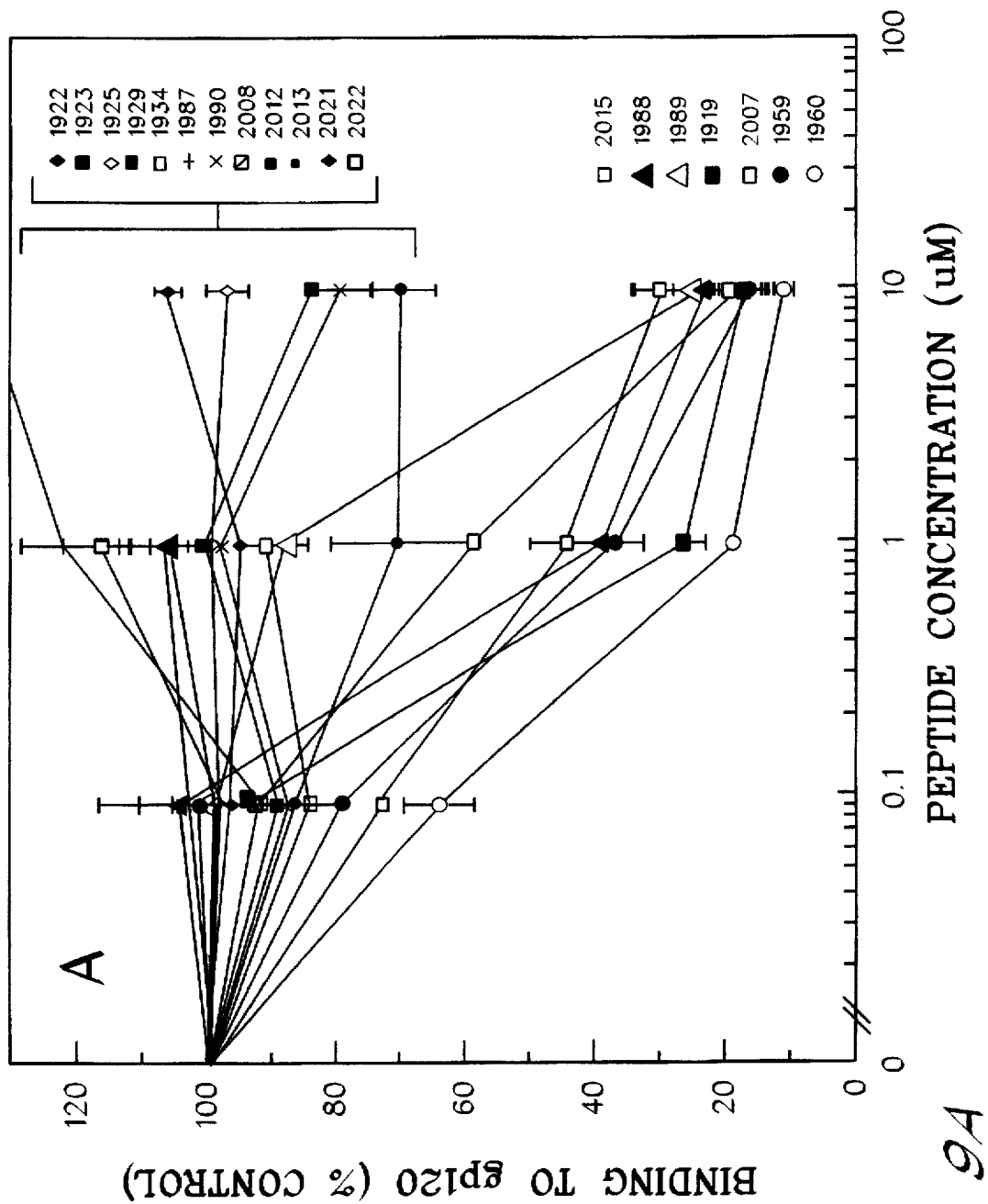
Figure 9B:
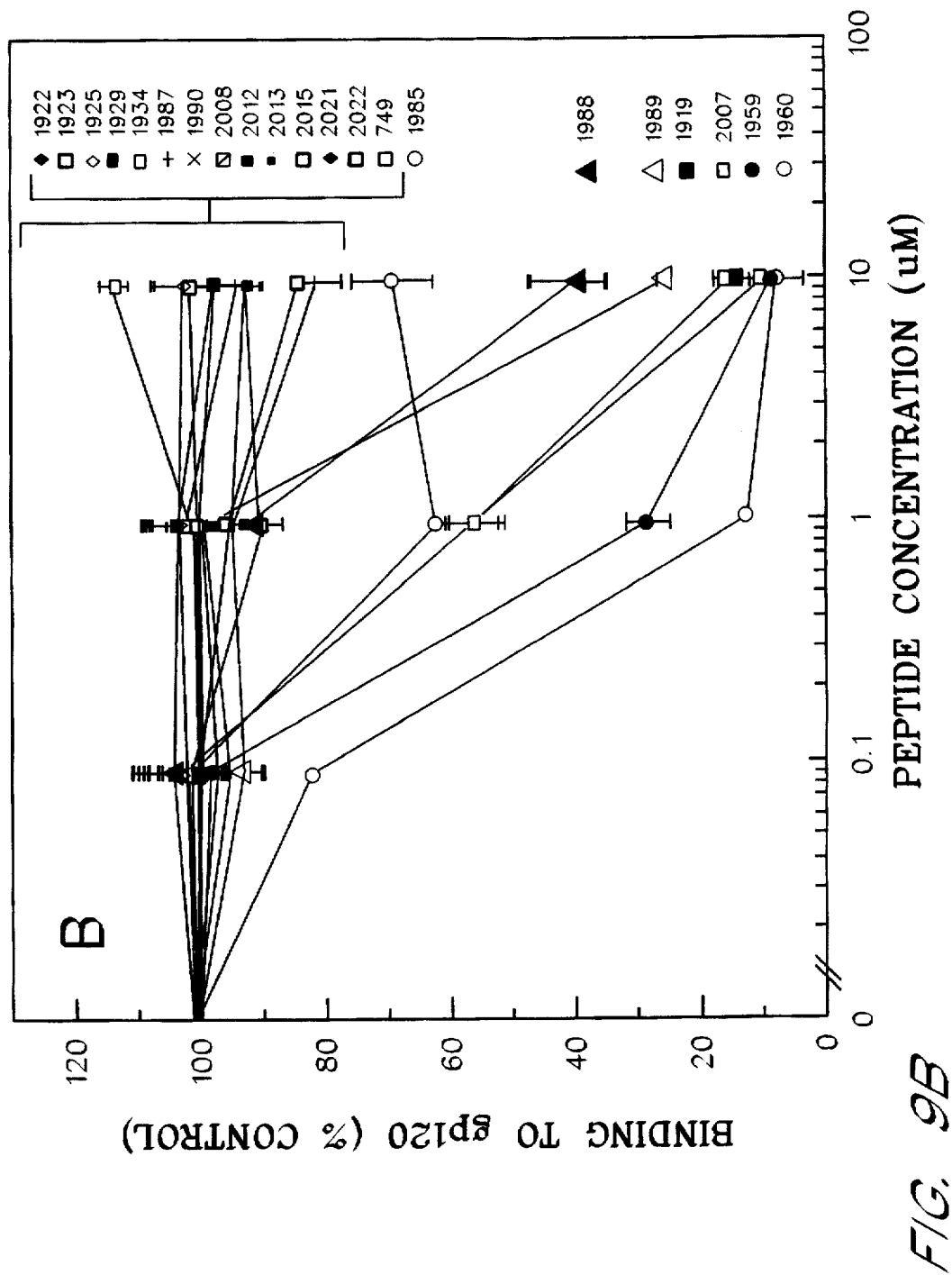

FIGS. 9A–B show graphic results for peptide competition of IgM binding to gp120. (A) Polyclonal serum IgM or (B) monoclonal IgM HEA was preincubated with each peptide at the indicated concentration, then assayed for binding to immobilized gp120 protein.

Figure 10:
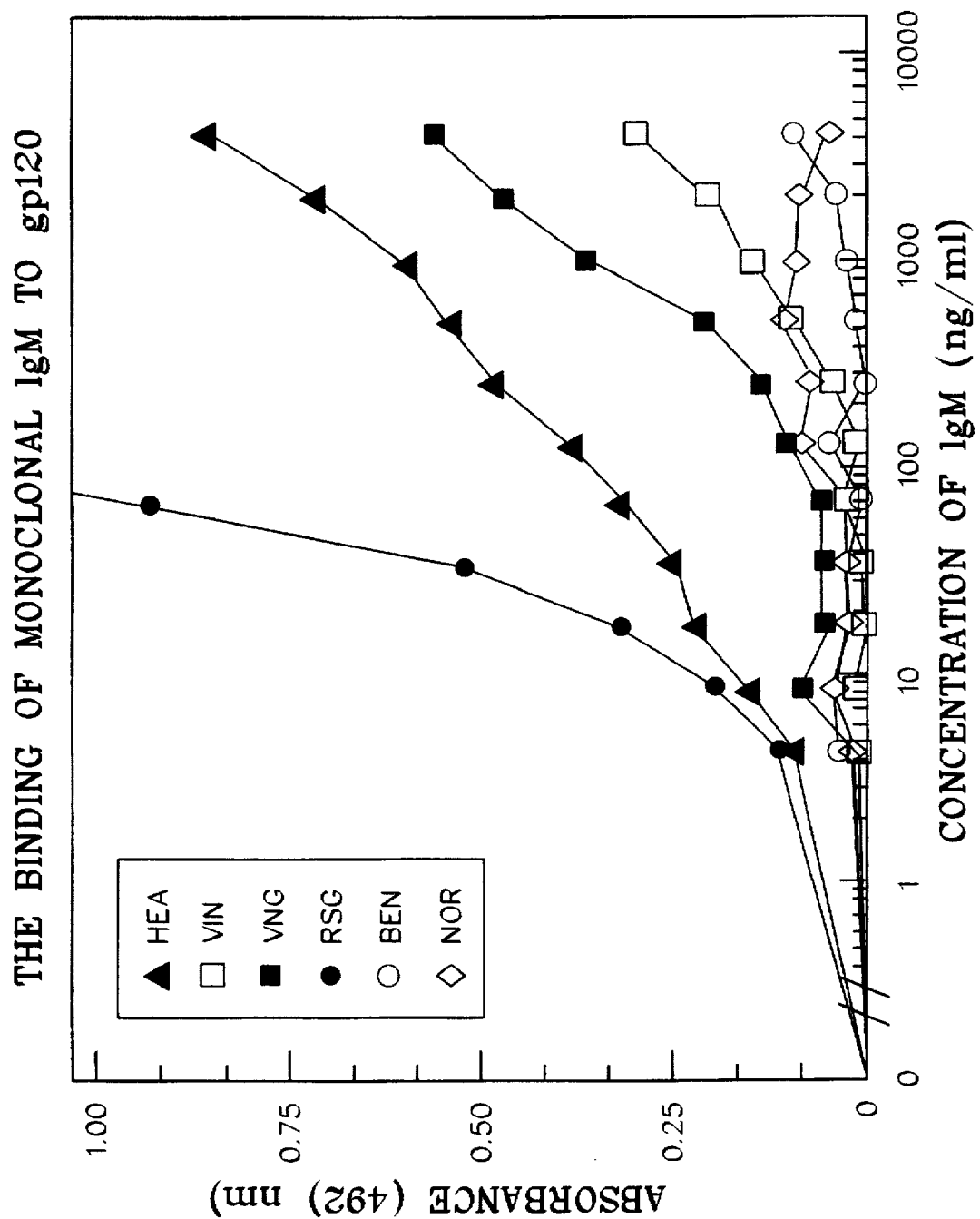

FIG. 10. Graph showing binding of monoclonal IgM to gp120. This figure shows examples of four Ig which significantly bound to gp120 (HEA, VIN, VNG, and RSJ), and two Ig which demonstrated no binding (BEN and NOR).

FIG. 11. Chart showing a comparison of the inhibitory activity of overlapping peptides. Overlapping peptides were compared for their ability to inhibit the biding of HEA to gp120. Such analysis revealed homologous decamer sequences (underlined) from the C2, C3, and C4 regions of gp120 which most likely account for the binding of peptides #1988/1989, #1589/2007, and #1959/1960.

Figure 12:
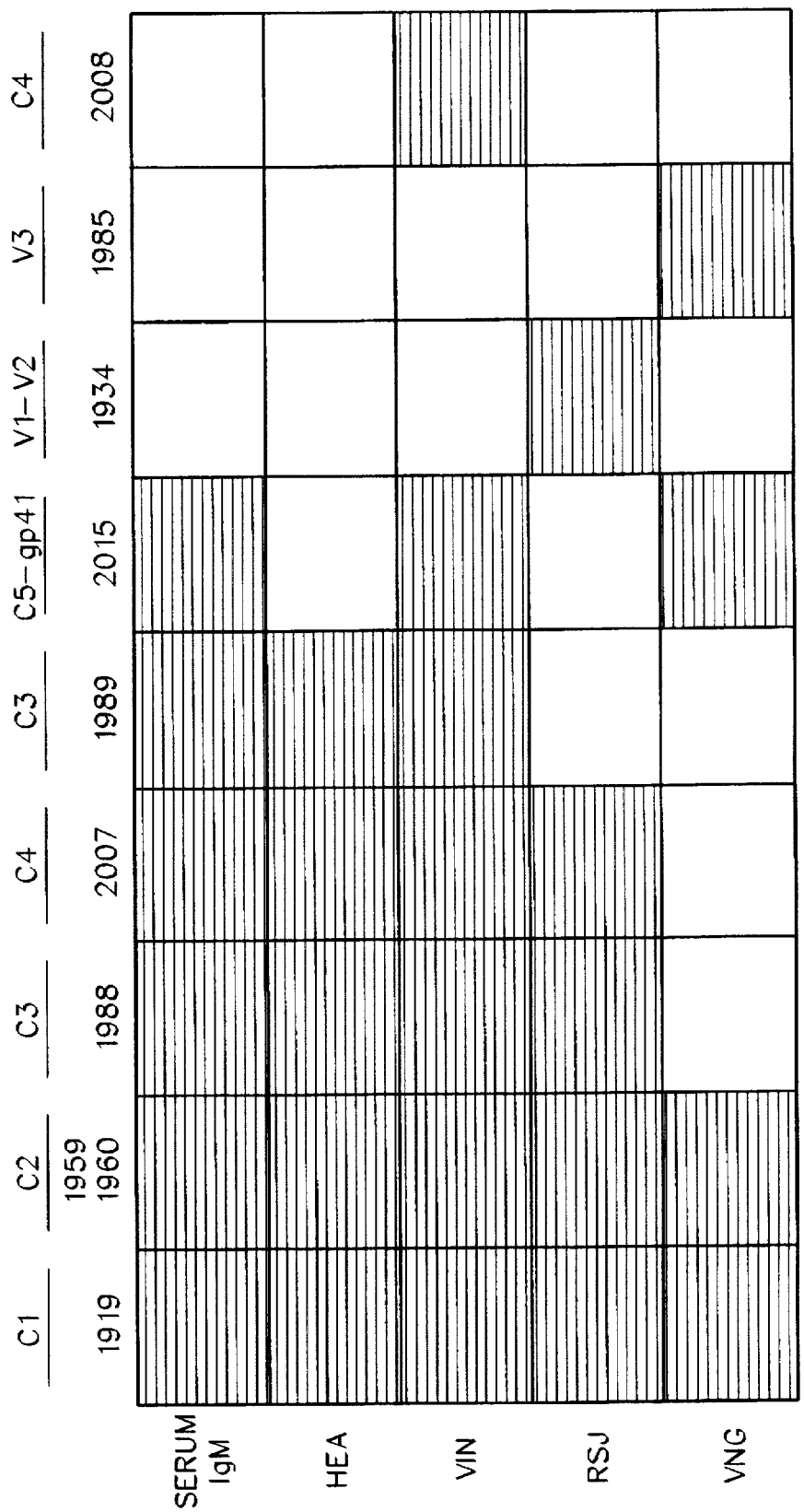

FIG. 12. Graphic summary of peptide fine specificities for a panel of independent Ig-SAg binding antibodies. A shaded box signifies that a peptide at 1.0 or 10 μM concentration inhibited binding >50%. Peptides #1959/1960, #1988/1989, and #2007/2008 are overlapping. The figure shows that peptides #1919, #1959, and #1960 bound to all Ig tested.

Figure 13:
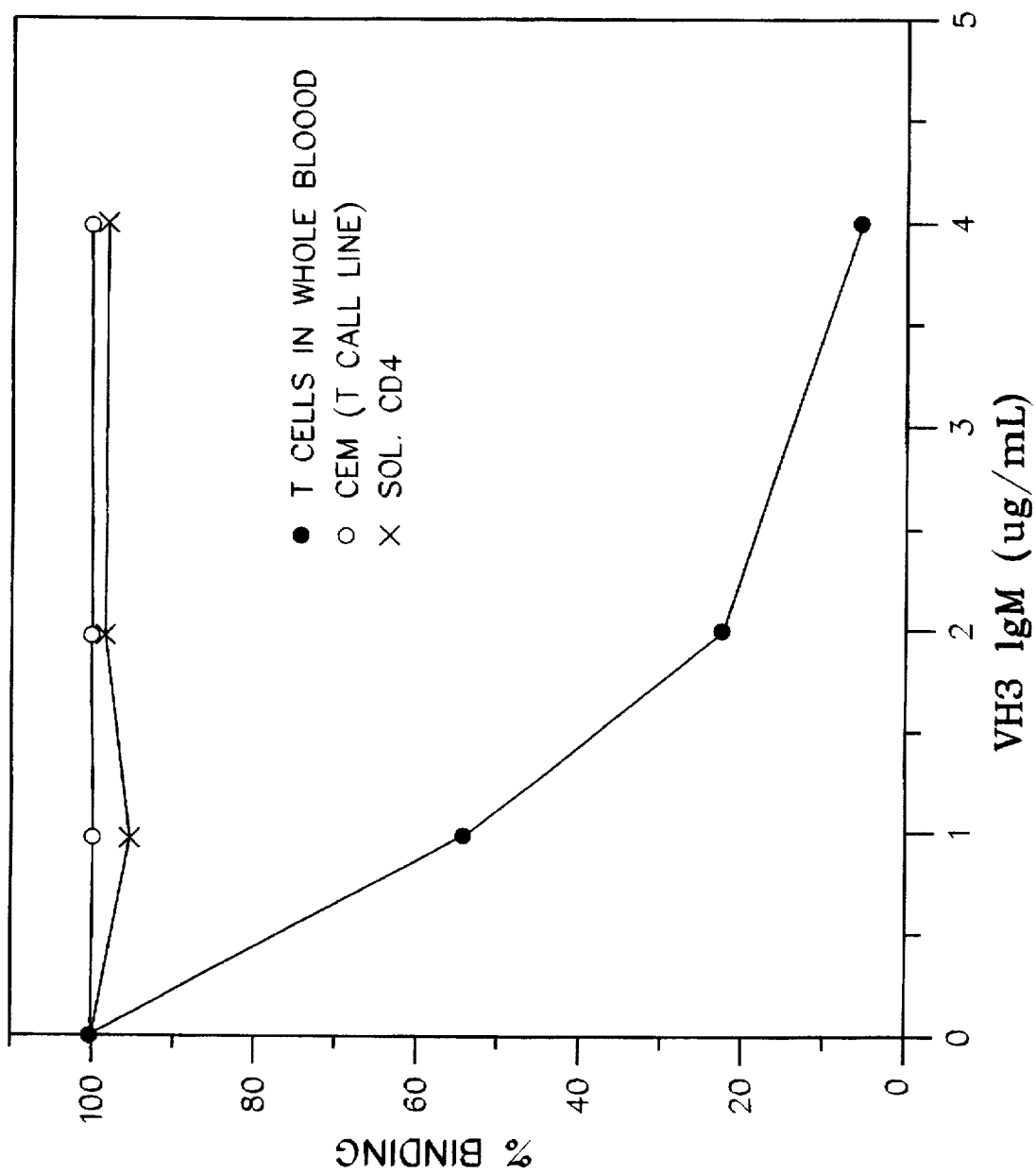

FIG. 13. Graph showing that VH3 IgM does not directly compete CD4 binding of gp120. ELISA and flow cytometry were used to study the inhibitory effect of VH3 IgM on the interaction between gp120 and either soluble CD4, CEM T-cells or T-cells that were present in a mixed population of cells obtained from whole blood.

Figure 14:
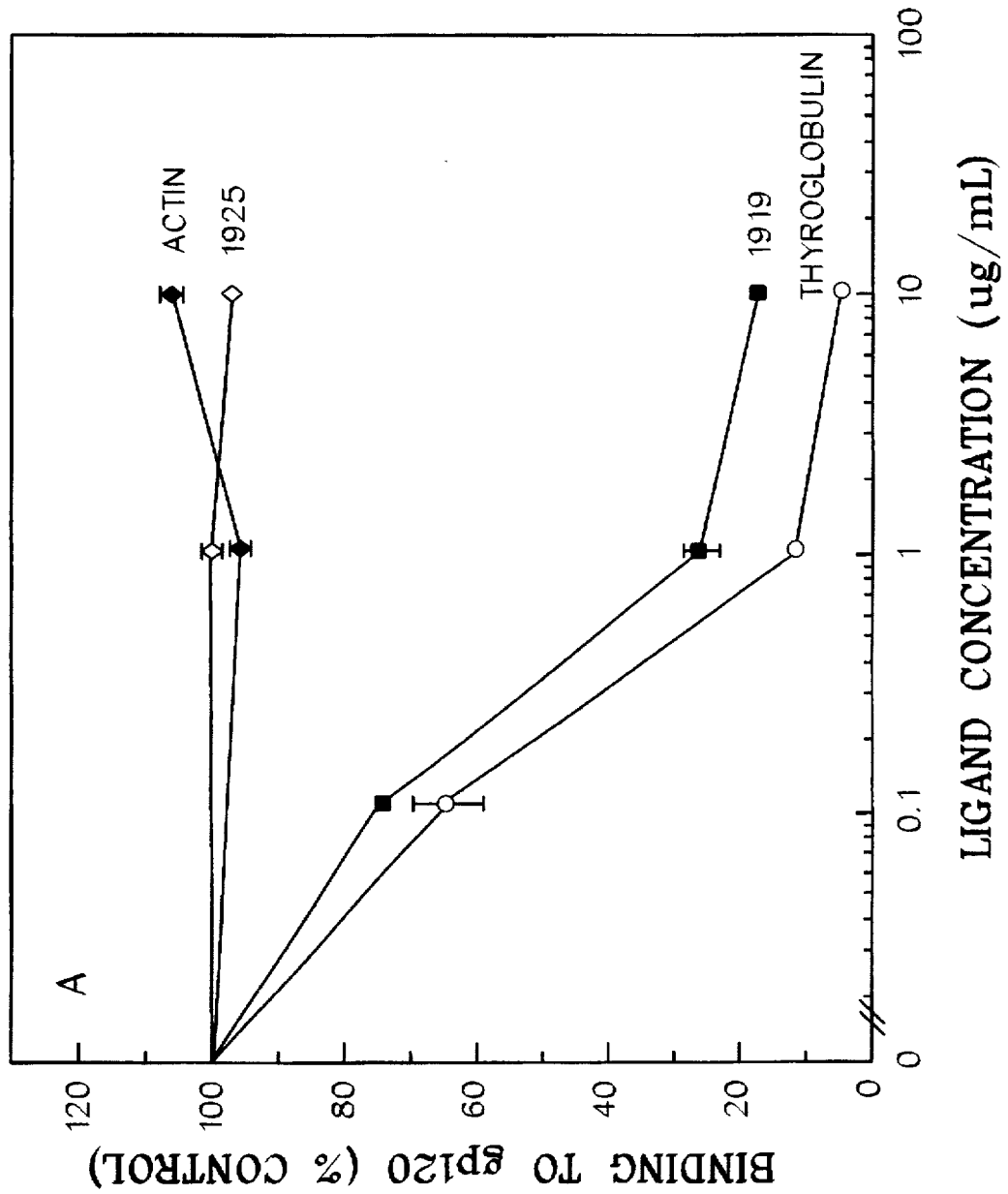

FIG. 14. Graph showing inhibition of the gp120 binding by VH3 IgM with a non-HIV superantigen (thyroglobulin). Two proteins (actin and thyroglobulin) and two synthetic peptides (1925 and 1919) were tested as inhibitors of gp120 binding to VH3 IgM in an ELISA assay.

SUMMARY OF THE INVENTION

One embodiment of the present invention is a method of inhibiting HIV infection in a patient at risk thereof. The method comprises administering to the patient a pharmacologically active dose of VH3 anti-gp120 antibody. Preferably, the administration of VH3 anti-gp120 antibody is done by intravenous infusion and the antibody is selected from either IgM antibody or IgG antibody. Most preferably, the anti-gp120 antibody is a multireactive immunoglobulin.

Another embodiment of the present invention is a method of inhibiting HIV infection in a patient at risk thereof. The method comprises administering to the patient an antigen in sufficient quantity to produce an immune response in the patient whereby antibodies that exhibit superantigen binding to gp 120 are produced. Preferably, the antigen comprises anti-gp120 IgM. More preferably, the antibodies that exhibit superantigen binding are either VH3 or VH4 antibodies. Alternatively, the antibodies that exhibit superantigen binding are either IgG or IgM antibodies.

Yet another embodiment of the present invention is a method of determining the HIV disease state of a patient infected with HIV. The method comprises obtaining a biological sample, preferably serum, from the patient, the sample containing antibodies, determining the level of antibodies with superantigen binding to gp120 in the sample, and comparing the determined level of the antibodies with a predetermined level of the antibodies in a biological sample from an asymptomatic HIV-infected patient, wherein a lower level in the biological sample from the patient relative to the predetermined level is indicative of a disease state more advanced than the asymptomatic HIV-infected patient. Preferably, the antibodies are VH3-containing antibodies and the VH3-containing antibodies are determined by binding to paraprotein B6. Alternatively, the antibodies could be VH4-containing antibodies.

Still another embodiment of the present invention is a method of determining the HIV disease state of a patient infected with HIV. This method comprises obtaining a biological sample from the patient, the sample containing blood mononuclear cells, determining the level of D12 +B cells in the sample, and comparing the determined level of the B cells with a predetermined level of the B cells in a biological sample from an asymptomatic HIV-infected patient, wherein a lower level in the biological sample from the patient relative to the predetermined level is indicative of a disease state more advanced than the asymptomatic HIV-infected patient.

A further embodiment of the present invention is a method for detecting the presence of a VH3 region on an immunoglobulin polypeptide. The method comprises: contacting the immunoglobulin polypeptide with the human immunodeficiency virus (HIV) gp120 protein, and determining whether the immunoglobulin polypeptide binds with the HIV gp120 protein, wherein detection of binding indicates that the immunoglobulin polypeptide has a VH3 region. Preferably, the immunoglobulin polypeptide is on the surface of a B-cell, most preferably wherein the B-cell is derived from the tonsil of a mammal. More preferably, the gp120 protein is labeled and the label is advantageously a radioactive label, a colorimetric label or a fluorescent label. Still more preferably, the HIV gp120 protein is HIV−1$_{SF2}$ rgp120. Advantageously, the determining step of this method is performed by flow cytometry.

An additional embodiment of the present invention is a method for suppressing HIV infection in a mammal, by the steps of: identifying a mammal infected with HIV and administering to the mammal a polypeptide having an immunoglobulin superantigen binding region against gp120, whereby HIV infection in the mammal is suppressed. Preferably, the polypeptide has a VH3 region and is a protein purified from a biological sample, most preferably serum. In a further preferred embodiment, the polypeptide has a VH3 region with fewer amino acids than the native full-length protein. Still more preferably, the administration is performed by one of the following methods: subcutaneously, intradermally, intravenously, intramuscularly, topically and intraperitoneally.

Another embodiment of the present invention is a method for immunizing a mammal against infection with HIV by administering to the mammal an immunoglobulin having a VH3 region in an amount sufficient to raise an antigenic response to VH3 in the mammal. Advantageously, the immunoglobulin is a polypeptide having fewer amino acids than a native, full-length protein. In a preferred embodiment, the immunoglobulin is expressed on the surface of a vaccinia virus, and the administering step of this method comprises administering the virus to the mammal. The administration can most preferably proceed by one of the following methods: subcutaneously, intradermally, intravenously, intramuscularly, topically or intraperitoneally.

Yet another embodiment of the present invention is a method for inhibiting HIV infection of a mammal by identifying a mammal in need of treatment for HIV infection, and administering to the mammal a pharmacologically active compound that suppresses the expression of VH3 immunoglobulins by lymphocytes, whereby HIV infection is inhibited. Preferably, the compound is an immunosuppressive agent, most preferably a kinase inhibitor or cyclosporine. Alternatively, the compound is preferably an anti-receptor antibody which binds to a membrane protein. Even more preferably, the antibody binds to one of the following antigens: B7, CD28, CD72 or CD5. Still even more preferably, the compound is an anticytokine antibody, most preferably IL-6 or TGF-β.

Another embodiment of the present invention is a transgenic mouse comprising a mouse that has human anti-gp120 VH3 IgM immune system.

Another embodiment of the present invention is a method for identifying an effective treatment for HIV infection in vivo, by administering HIV to a transgenic mouse with a human anti-gp120 VH3 immune system, then incubating the HIV in the mouse until infection of HIV develops, and thereafter treating the mouse with a treatment suspected of being effective against HIV infection in vivo, and finally determining whether the treatment was effective in treating HIV infection of the mouse.

An additional embodiment of the present invention is a method for inhibiting HIV in an HIV-infected patient by administering to the patient a pharmacologically active dose of anti-gp120 VH3 antibodies such that the antibodies cause a clonal deficiency of B-cells expressing the anti-gp 120 VH3 antibodies.

A further embodiment of the present invention is a method for producing a murine model for studying HIV infection in vivo, by injecting a neonatal mouse with a solution comprising HIV, incubating the solution in the mouse until an HIV infection develops, wherein the infection is propagated by the B cells of the mouse. One most preferable embodiment of the present invention includes an HIV-infected mouse produced this method.

DETAILED DESCRIPTION

We have discovered that the gp120 viral envelope glycoprotein is a superantigen for immunoglobulins. Specifically, we found that gp120 has a strong affinity for VH3 type immunoglobulins. However, we also found that some VH4 type immunoglobulins exhibit similar binding characteristics. We believe this discovery will illuminate the process by which HIV infection results not only in the depletion of T-cells expressing CD4, but also of B-cells that express immunoglobulin (Ig) VH3 products.

We have also discovered that a subpopulation of normal B-cells from non-HIV infected individuals binds to gp120 via membrane Ig. Most of these B-cells expressed Ig VH3 family genes. In addition, a subset of normal serum IgM bound to gp120, the majority of which also bound to *S. aureus* protein A, a known VH3 Ig superantigen. These results, in combination with those previously discussed, indicate that immunoglobulin molecules have a superantigen-binding region that represents a second cellular ligand for gp120. This suggests a mechanism for HIV infection of B-cells. Although it appears that the majority of immunoglobulins having this binding region are VH3 type, other Ig types, such as VH4, should be considered to be within the scope of this invention.

Using a cell-free assay, we showed that gp120 selectively bound soluble Ig that was present in a fraction of normal serum enriched for the VH3 Ig family. The VH3 family is also characterized by binding to protein A and a limited but structurally diverse set of antigens. Additionally, we have successfully isolated clonal B-cell lines expressing VH3 Ig for monoclonal antibody production and V gene isolation. Experiments using these cell lines have provided evidence that VH3 family antibodies neutralize HIV infection in vitro.

These findings are relevant to HIV pathogenesis. The B-cell population undergoes significant functional derangement during HIV infection, attributed in part to T cell and cytokine abnormalities. The results of the present invention suggest that the receptor-mediated binding of HIV or soluble gp120 to the large VH3 B-cell population (20–30% of total B-cells) contributes to B-cell disorders during HIV infection.

Interactions between gp120 and naturally occurring Ig were found to have several features characteristic of superantigen binding. Previously discovered T cell superantigens normally bound to the β chain of the T cell receptor (TCR) and to major histocompatibility complex (MHC) class II proteins outside the antigen binding groove (P. Marrack and J. Kappler, *Science* 248: 705 (1990)). Superantigen binding has also been correlated with the initial stimulation and subsequent depletion of a relatively large population of T cells expressing specific TCR β chains. Analogously, gp120 binds to a subpopulation of B-cells and serum Ig that is much larger than expected for an antigen-specific humoral response, and predominates with a specific immunoglobulin V gene family (VH3). Due to the complementarity-determining region (CDR) diversity between VH3 family members, the immunoglobulin superantigenobinding region for gp120 is believed to lie within the first or third framework regions (P. M. Kirkham, F. Mortari, J. A. Newton, and H. W. Schroeder, EMBO J. 11:603 (1992)).

We have further discovered a correlation between gp120 binding to VH3 and the observed deficit of VH3-expressing B-cells in AIDS patients. Indeed, the present invention reports the first correlation of superantigen binding with a functional consequence in vivo, i.e., VH3 B-cell depletion.

The mechanism for superantigen-induced clonal deletion of T cells in secondary lymphold tissue is uncertain. However, a variety of proposed mechanisms are applicable to the B-cell. For example, asynchronous signalling or immunoregulatory effector cells are possibilities. In addition, it should be emphasized that HIV-related depletion of VH3 Ig cells could involve any of the processes already proposed for CD4 T cell depletion, along with other proposed mechanisms for B-cell clonal abnormalities in HIV infection.

Another explanation for the observed binding of normal serum Ig to gp120 might be that the VH3 Ig subset is multireactive. Herein we use the terms multireactive and polyreactive as synonyms. The existence of naturally occurring multireactive VH3 type antibodies is well documented. Differentiation between the superantigen and multireactive models requires further functional characterization of the VH3 B-cell response to HIV, and structural definition of the binding domains in the gp120 and IgM polypeptides.

Example 1 illustrates the method used to detect the interaction between HIV gp120 and a subpopulation of normal B-cells.

EXAMPLE 1

HIV gp120 Binding to B-cells

Mononuclear cells from fresh tonsil tissue were obtained from 7 subjects aged 2–14 years as described below. All donors were HIV seronegative. Tonsil cells were incubated with recombinant gp120 (rgp 120) from HIV–$1_{SF2}$ (expressed in CHO cells), stained with antisera to HIV–$1_{SF2}$rgp120 and lineage-specific markers, and analyzed by flow cytometry.

The tonsil cells were obtained from anonymous tonsillectomy specimens under authorization from the UCLA Human Subjects Protection Committee. Mononuclear cells were isolated and resuspended in Hanks'salts with 2% heat inactivated fetal calf serum, 10 mM HEPES, and 0.02% sodium azide. Cell viability was assessed by trypan blue exclusion and only cell populations with >95% viability were used. Cells were then prepared for flow cytometry analysis by the following modifications. $5\times10^5$ cells were incubated with 4 µg/ml of HIV$1_{SF2}$ rgp120 (expressed in Chinese hamster ovary cells) (AIDS Research and Reference Reagent Program, Division of AIDS, NIAID, NIH: catalogue #386) for 30 minutes at 4° C. In one experiment (data not shown), non-glycosylated gp120 was used (from HIV–$1_{SF2}$, expressed in yeast; NIH catalog #388). Cells were incubated 30 minutes (4° C.) with antiserum to HIV–$1_{SF2}$ gp120 (NIH catalogue #385) and subsequently with one or more of the following: swine anti-goat IgG-phycoerythrin (PE) (CALTAG, So. San Francisco. Calif.), anti-CD19-FITC, anti-CD20-FITC, and anti-CD3-FITC (BECTON DICKINSON, Sunnyvale, Calif.). In some experiments, cells were incubated with the VH3-associated anti-idiotype murine monoclonal antibodies B6, D12 and 16/6. Cells were analyzed using a FACScan® flow cytometer.

Dead cells were excluded based on forward and side scatter and by using the dead cell discriminator 7-amino-actinomycin-D (I. Schmid, W. K. Krall, C. H. Uittenbogaart, J. Braun, and J. V. Giorgi, Cytometry 13: 204 (1992)). Control samples were processed similarly with the omission of gp120 and/or substitution of a FITC-conjugated isotype control antibody. Results show the fluorescence intensity of 5000 live cell events.

In all seven subjects, 3–6% of the B-cell population (CD19+) bound gp120 (FIG. 1A). T-cells in the tonsil served as an internal control for gp120 binding. As expected, 65% of the T-cell (CD19−, CD3+) population bound gp120, consistent with the known abundance of CD4 T-cells (FIG. 1A). In some experiments, tonsils were initially depleted of T-cells by erythrocyte rosetting. This well-known procedure is described by S. V. Hunt in "Preparative immunoselection of lymphocyte populations"; in L. A. Herzenberg's *Handbook of Experimental Immunology*, Blackwell Scientific Publications, Boston, 1986, Volume 2, Chapter 55, the disclosure of which is hereby incorporated by reference. This procedure did not diminish the population of CD19+ cells binding gp120.

This result prompted us to evaluate the surface receptor responsible for binding of gp120 in the B-cell subpopulation. CD4 is the primary known receptor for gp120. Although normal B-cells do not express CD4, it was conceivable that a small population of B-cells might express this molecule. However, we were unable to detect CD19+ tonsil cells after staining with the anti-CD4 antibody Leu3a.

Figure 1B:
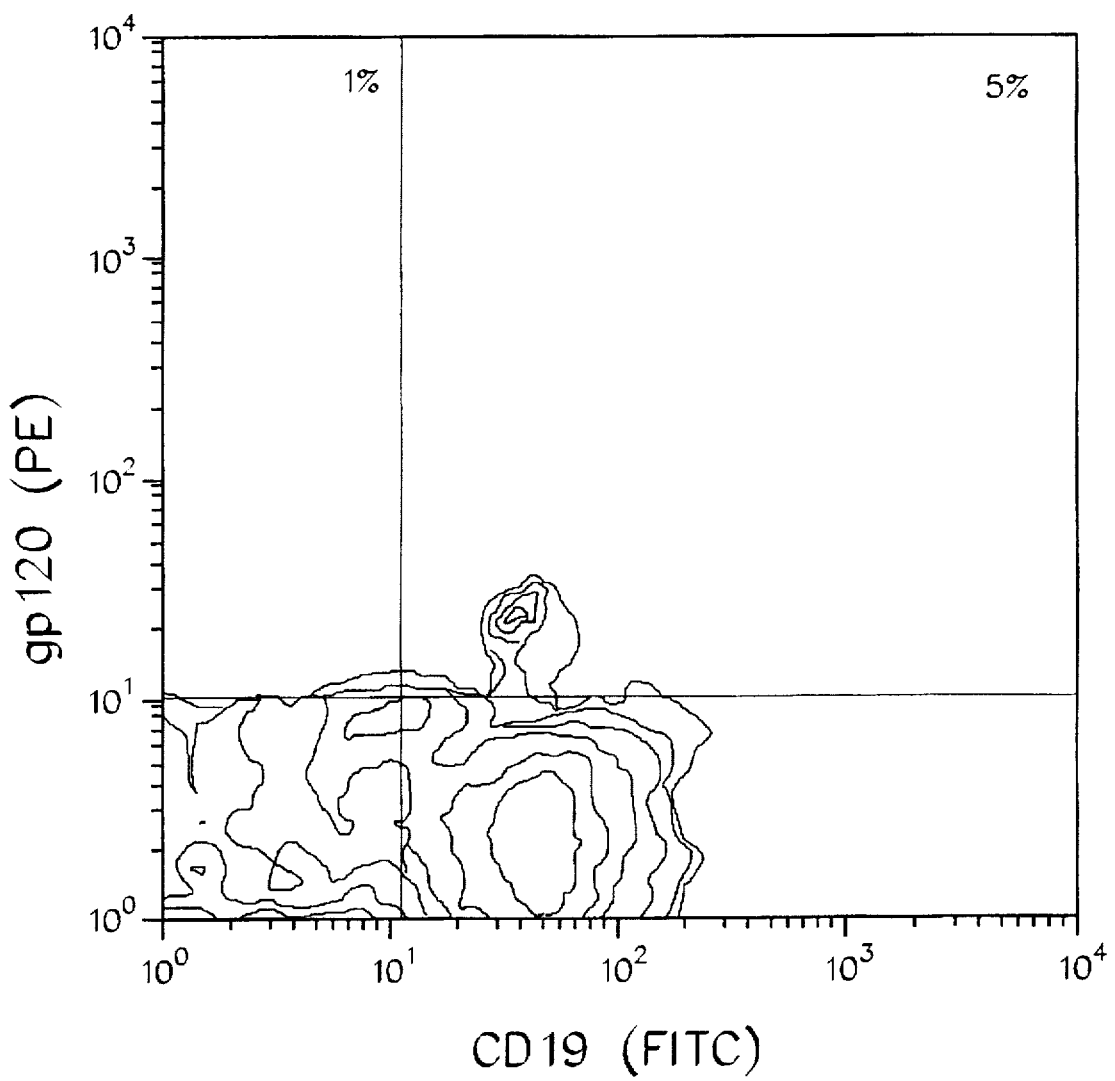

Leu3a is an antibody known to block binding of gp120 to CD4. Accordingly, pretreatment of tonsil cells with Leu3a completely inhibited gp120-binding by tonsil T-cells (FIG. 1B). In contrast, Leu3a did not inhibit binding of gp120 to the subpopulation of CD19+ cells (FIG. 1B), showing that gp120 did not bind to the B-cells via CD4. Consistent with these results, we also observed that a similar B-cell subpopulation also bound nonglycosylated HIV–$1_{SF2}$ rgp120 produced in yeast, a form of gp120 that does not bind CD4 (data not shown).

Figure 1C:
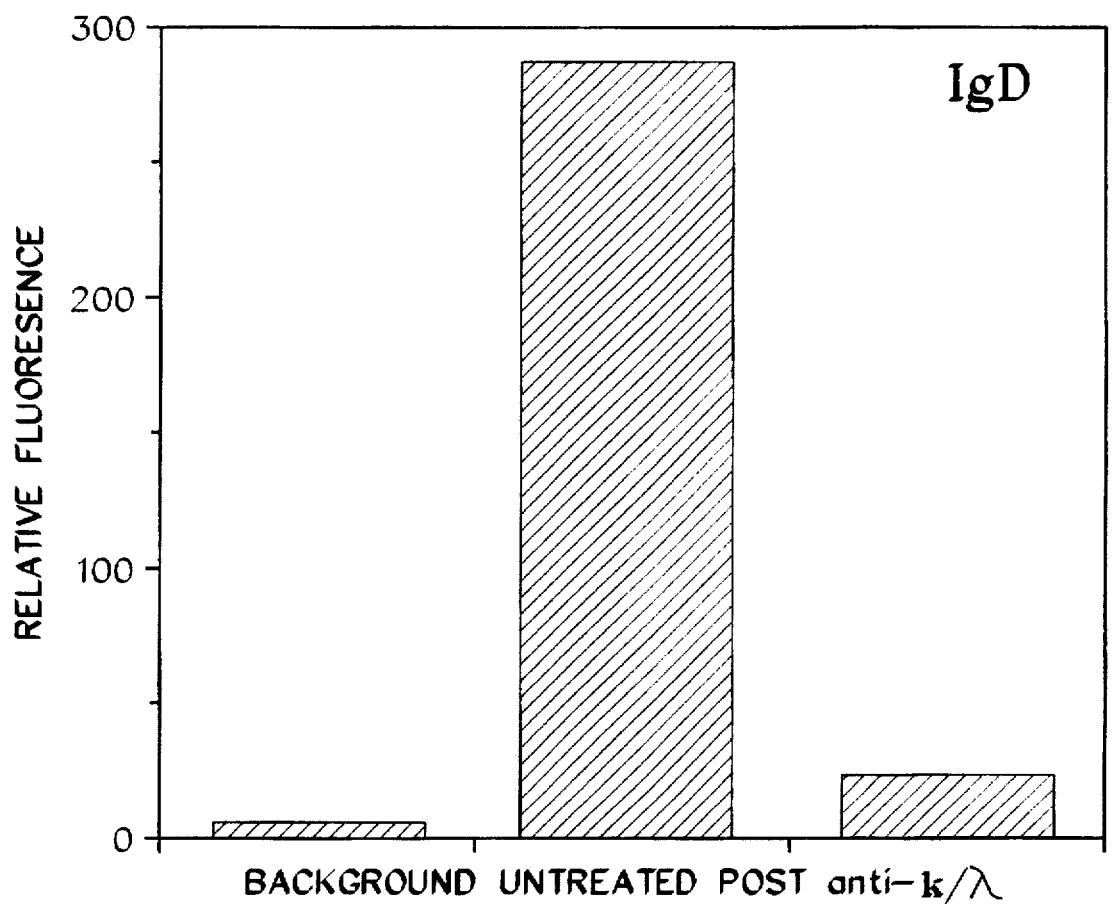
Figure 1D:
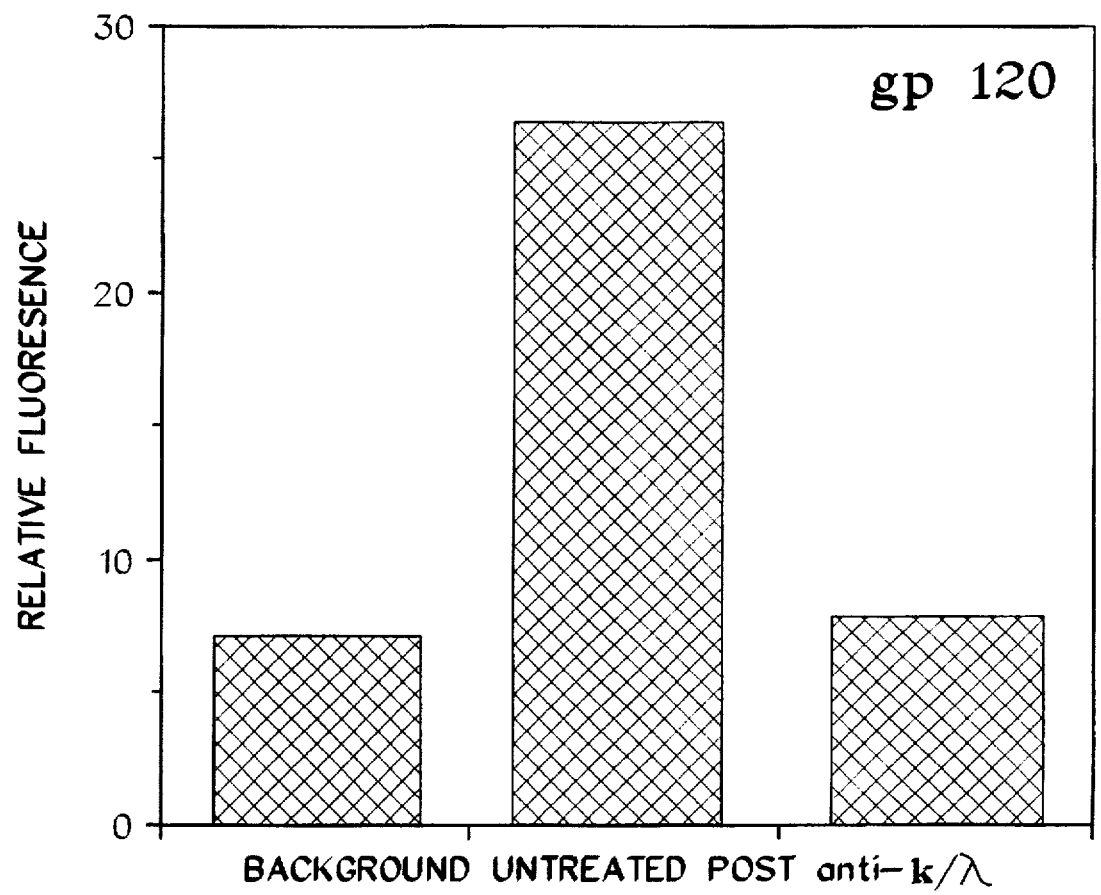

The CD4-independent binding of gp120 to this population of normal B-cells implied that a second cellular ligand for gp120 existed on these selected cells. We postulated that gp120 bound to these cells via membrane Ig. To test this theory, cell surface Ig was selectively removed by pretreating tonsil cells with anti-K and anti-λ Ig light chain antibody before the gp120 binding assay. Endocytosis of membrane Ig caused by treatment of anti-Ig antibody has been shown to decrease surface Ig by >90% (K. A. Ault and E. R. Unanue, *J. Immunol.* 119:327 (1977)). In the present experiments, such treatment removed 94% of membrane IgD (FIG. 1C). Following removal of membrane Ig, a corresponding amount of gp120-binding was lost (FIG. 1D). This result indicated that gp120 binding depended on the presence of membrane Ig.

Example 2 describes the method used to determine whether the B-cells which bound gp120 expressed VH3 Ig. Three anti-VH3 idiotype antibodies —B6, D12, and 16/6 were employed in this procedure. These anti-VH3 antibodies detect homologues of the 56pl and 30pl VH3 genes, together numbering approximately 10 germline VH genes (T. Olee et al., *J. Clin. Invest.* 88:193 (1991); M. A. Walter, H. M. Dosch, and D. W. Cox, *J. Exp. Med.* 174:335 (1991)).

EXAMPLE 2

Demonstration of gp120 Binding to VH3

Tonsil B-cells from four normal subjects were stained for CD19, gp120, and VH3 idiotopes, then analyzed by flow cytometry, gating on either all CD19+ cells ("all B-cells") or CD19+,gp120-binding cells ("gp120+ B-cells"). Results are shown in Table 1 as the average±standard deviation of % positive cells for the four subjects.

An overabundance of VH3 idiotope-positive B-cells was detected in gp120-binding cells, and these three idiotopes alone accounted for 72% of the gp120-binding B-cell population.

TABLE 1

| Predominance of VH3 idiotopes in gp120-binding B-cells | | |
|---|---|---|
| Idiotope | All B-cells | gp120+ B-cells |
| 16/6 | 16% ± 2% | 26% ± 2% |
| B6 + D12 | 12% ± 1% | 46% ± 3% |

To confirm the identity of this population of B-cells, we examined binding of gp120 by Epstein Barr Virus-transformed tonsil cells.

Example 3 describes one method used to detect the interaction between gp120 and B cells.

EXAMPLE 3 gp120 Binding to EBV-Transformed Tonsillar Cells

Freshly isolated, T-cell-depleted tonsillar mantle zone cells were infected with Epstein-Barr virus (EBV) and expanded in culture for three weeks. The T-cells were removed by erythrocyte rosetting.

T-cell-depleted mononucleartonsil cells were sorted into germinal center (Leu-17$^{bright}$, IgD$^{dim}$) and mantle zone (IgD$^{bright}$, Leu-17$^{dim}$) subpopulations using a FACSTAR$^{plus}$ cell sorter (Becton Dickinson) and transformed with EBV. After expansion in culture for 3 weeks, the EBV-transformed mantle zone B-cells were stained with labeled gp120 and FACS-sorted into subpopulations of those that bound and those that did not bind gp120. The sorted cells were again expanded in culture for 3 weeks, and then reanalyzed for gp120 binding.

Figure 2A:
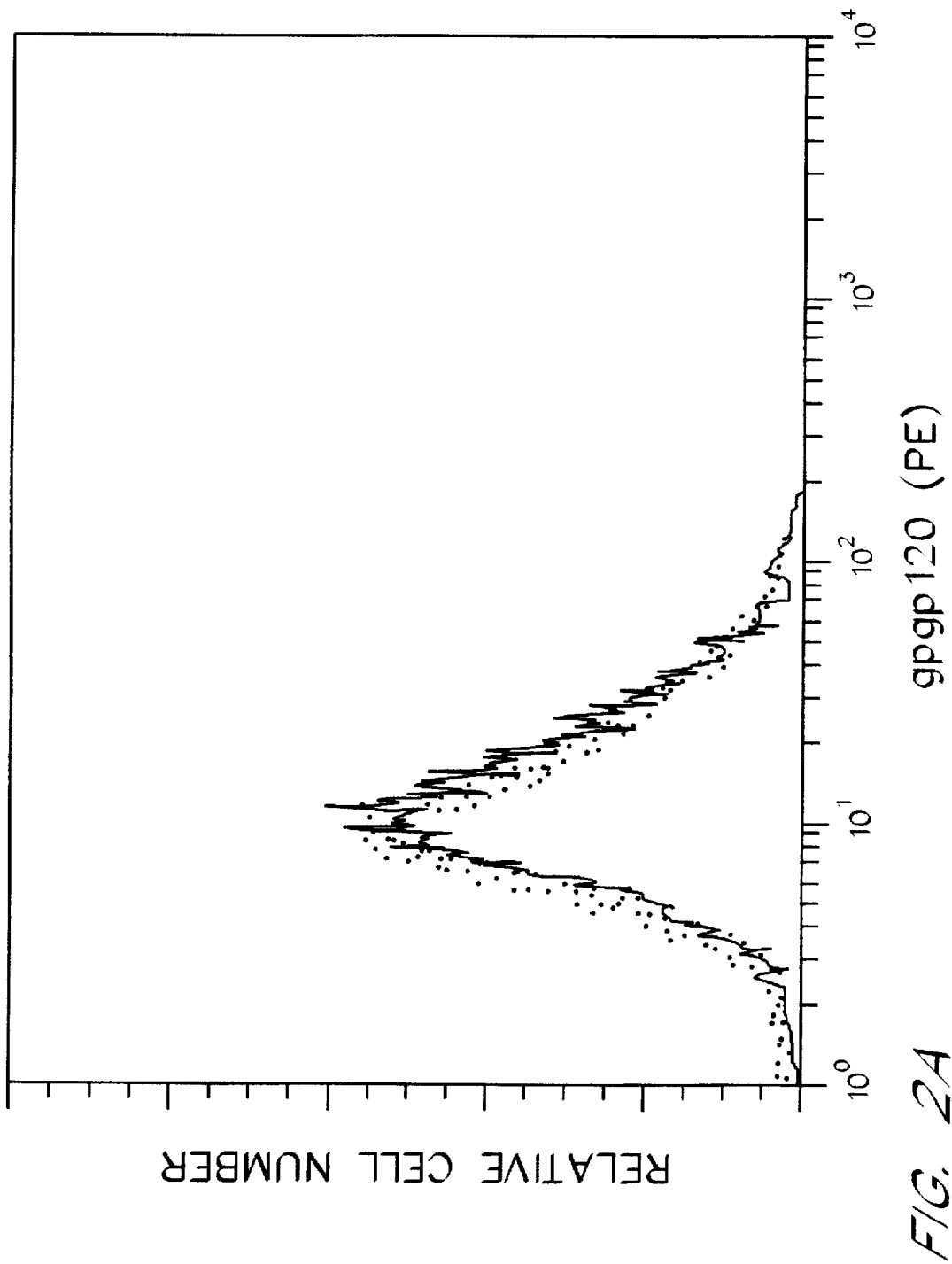
Figure 2B:
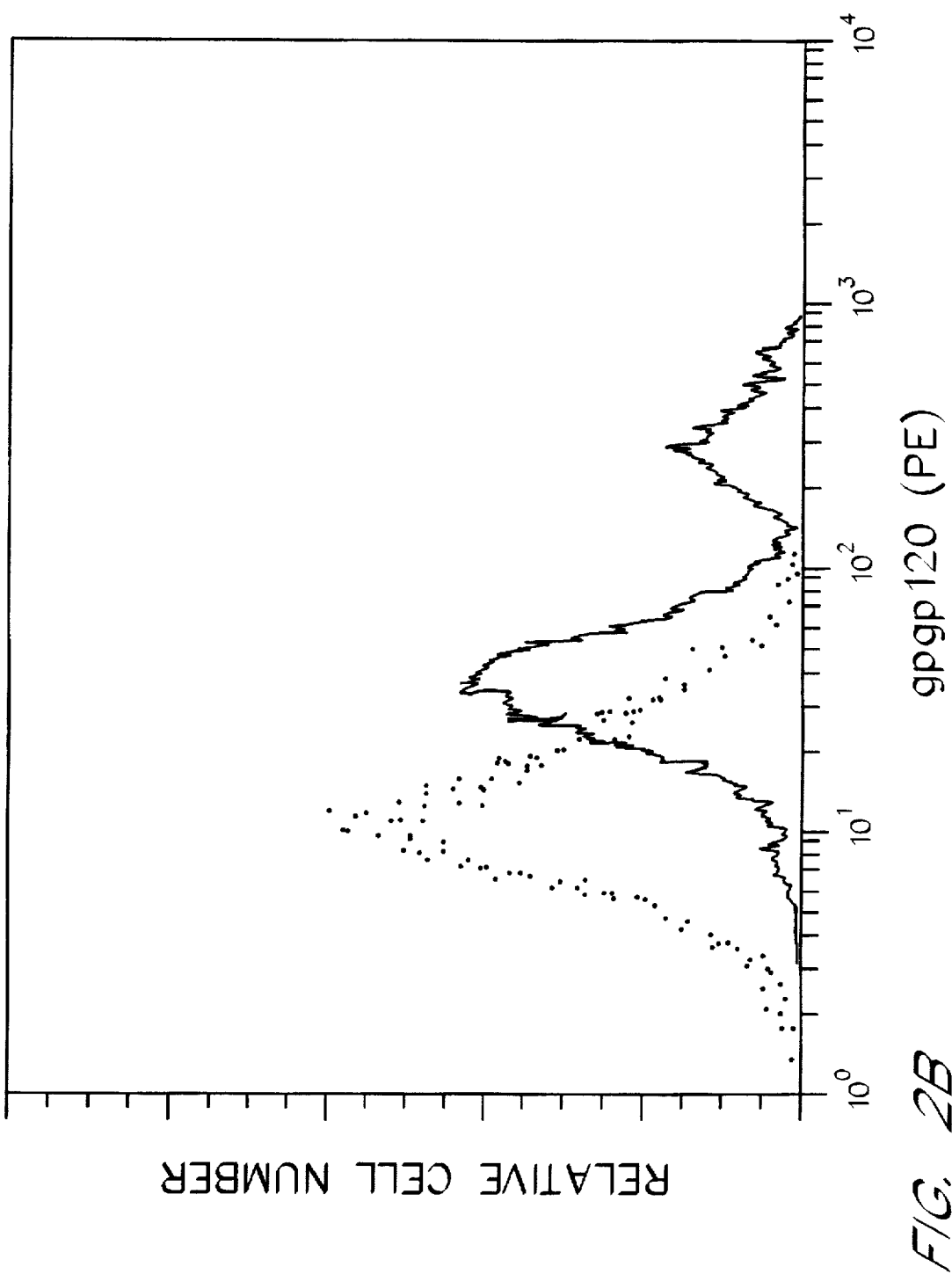

After this round of FACS sorting, 1.5% of the population was found to bind gp120. When reanalyzed after three weeks in culture, the original gp120 non-binding population still did not bind gp120 (FIG. 2A). In contrast, 18% of the original gp120-binding population stained brightly for gp120 while 53% of the population stained more dimly (FIG. 2B). It is also notable that EBV-transformed tonsil germinal center cells lacked detectable binding to gp120, consistent with the known normal deficit of near-germline VH3 B-cells in this differentiated state.

It should also be appreciated that while this provides one method of detecting binding of gp120 to B-cells, other methods known to those with skill in the art are also within the scope of the present invention. These methods could include for instance, radiolabeling or colorimetrically labeling gp120 and contacting B-cells in-vitro. Assaying for label attached to the B-cells would provide a method for determining binding.

Example 4 demonstrates the method used to prove that an Ig which is ordinarily present in the serum of HIV seronegative individuals could bind gp120. In this example, we evaluated binding of Ig to gp120 in a cell-free system using an enzyme-linked immunosorbent assay (ELISA).

EXAMPLE 4

Cell-Free Binding of Ig to gp120

ELISA microtiter plates (COSTAR, Cambridge, Mass.) were coated overnight (4° C.) with 50 ng of gp120, and diluted in carbonate-bicarbonate buffer, pH 9.6 (SIGMA, St. Louis, Mo.). The plates were rinsed 3× for 15 minutes with PBS+0.5% Tween-20, incubated for 1 hr. (25° C.) with normal serum, protein A-enriched or -depleted fractions, or IgM paraproteins diluted in PBS+0.5% Tween-20, and stained for 1 hr. (4° C.) with goat anti-human IgM- or IgG-horseradish peroxidase (HRP) (Southern Biotechnology Associates, Birmingham, Al.).

Qualitatively similar results were obtained if 3% nonfat milk or 1–5 mg/ml BSA was used instead of Tween-20. Samples were incubated with 50 µl of o-phenylenediamine (OPD) dihydrochloride (Sigma) for 30 minutes (37° C.). 50 µl of 3-N H$_2$SO$_4$ was added and the absorbance was determined at 492 nm. The following controls had no binding or color reaction: (a) without serum, protein A fractions, or IgM paraproteins, (b) substitution of goat anti-human IgM-HRP with anti-mouse IgM-HRP, and (c) the absence of gp120 (i.e., secondary and tertiary antibodies did not bind to the ELISA plate in the absence of carbonate-bicarbonate buffer).

Other methods of labeling the serum antibodies also are anticipated to be within the scope of the present invention. For instance, radioactive, colorimetric, and fluorescent labels could also be used to identify binding of serum antibodies to gp120.

Figure 3A:
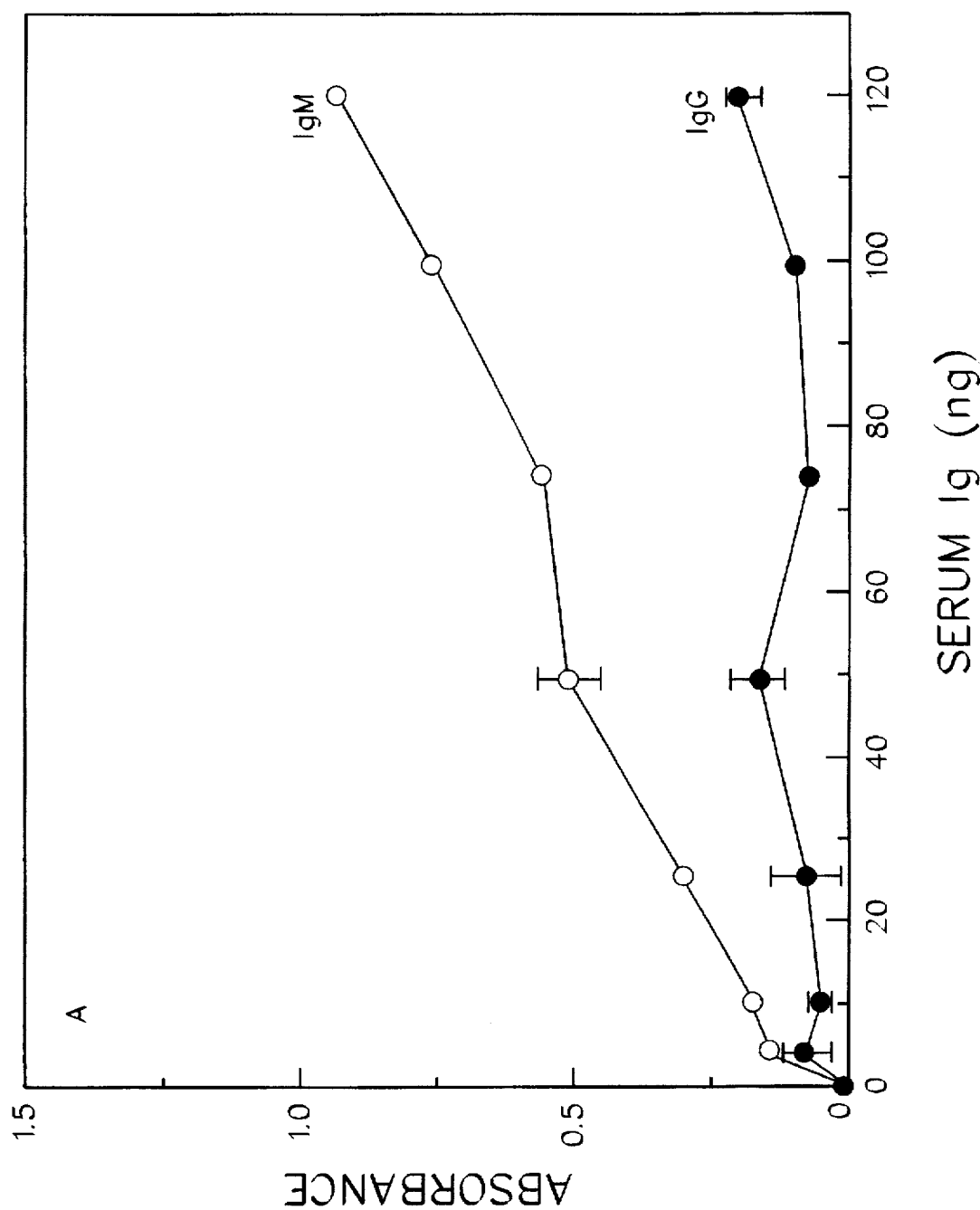

A dose-dependent binding of serum IgM to gp120 was detected using as little as 5–10 ng of serum IgM. In FIG. 3A, normal serum was assayed by the above ELISA method for binding with anti-IgM (○) and anti-IgG (●). The results demonstrate that IgM binding was approximately ten-fold greater than binding by IgG. Similar results were obtained utilizing a commercially available ELISA plate for detecting antibodies against a total HIV–1 lysate (Retro-tek® HIV–1 ELISA kit from Cellular Products, Inc. Buffalo, N.Y.). Using this ELISA plate, binding was readily detectable for normal serum IgM, but not for IgG, the isotype routinely assayed by this kit (data not shown). This demonstrated that gp120 has a much higher affinity for IgM than for IgG.

The following additional experiments ruled out artifactual binding due to ELISA conditions: (1) an immuno-dot blot assay was performed by standard methods where gp120 was blotted onto nitrocellulose and the subsequent Ig binding reactions were each performed at neutral pH; and (b) the HEA-gp120 K$_D$ determination demonstrated liquid phase binding of antibody and antigen.

Serum was collected from normal, seronegative individuals with no history of HIV contact. Normal serum samples from HIV seronegative individuals were obtained from anonymous specimens of the UCLA blood donor facility under authorization of the UCLA Human Subjects Protection Committee. Six different serum samples tested displayed similar gp120-binding activity in our assay conditions. IgM paraprotein samples were negative for IgG-specific HIV reactivity as tested by the UCLA clinical laboratories.

Example 5 describes the method used to test the relationship between the gp120-binding IgM subset of antibodies and the VH3 family of antibodies. This was simply investigated by testing whether the fraction of IgM which bound S. aureus protein A was the same fraction of IgM which bound gp120. Protein A preferentially binds VH3 heavy chain molecules.

EXAMPLE 5

S. aureus Binding to IgM

IgG was removed from normal, HIV seronegative serum using a Quik-Step IgM r-protein G affinity resin kit (ISOLAB, Akron, Ohio). IgG-depleted normal serum was separated into bound ("protein A +") and unbound ("protein A$^{−}$") fractions by protein A affinity chromatography (PIERCE, Rockford, Ill.) with the following modifications to the manufacturer's procedure: the binding and elution buffers described by Sass et al. were used (E. H. Sasso, G. J. Silverman, and M. Mannik, *J. Immunol.* 143:2778 (1989); E. H. Sasso, G. J. Silverman, and M. Mannik, *J. Immunol.* 147:1877 (1991)), these reference being incorporated herein by reference. Additionally, the samples were passed over the protein A column twice.

Figure 3B:
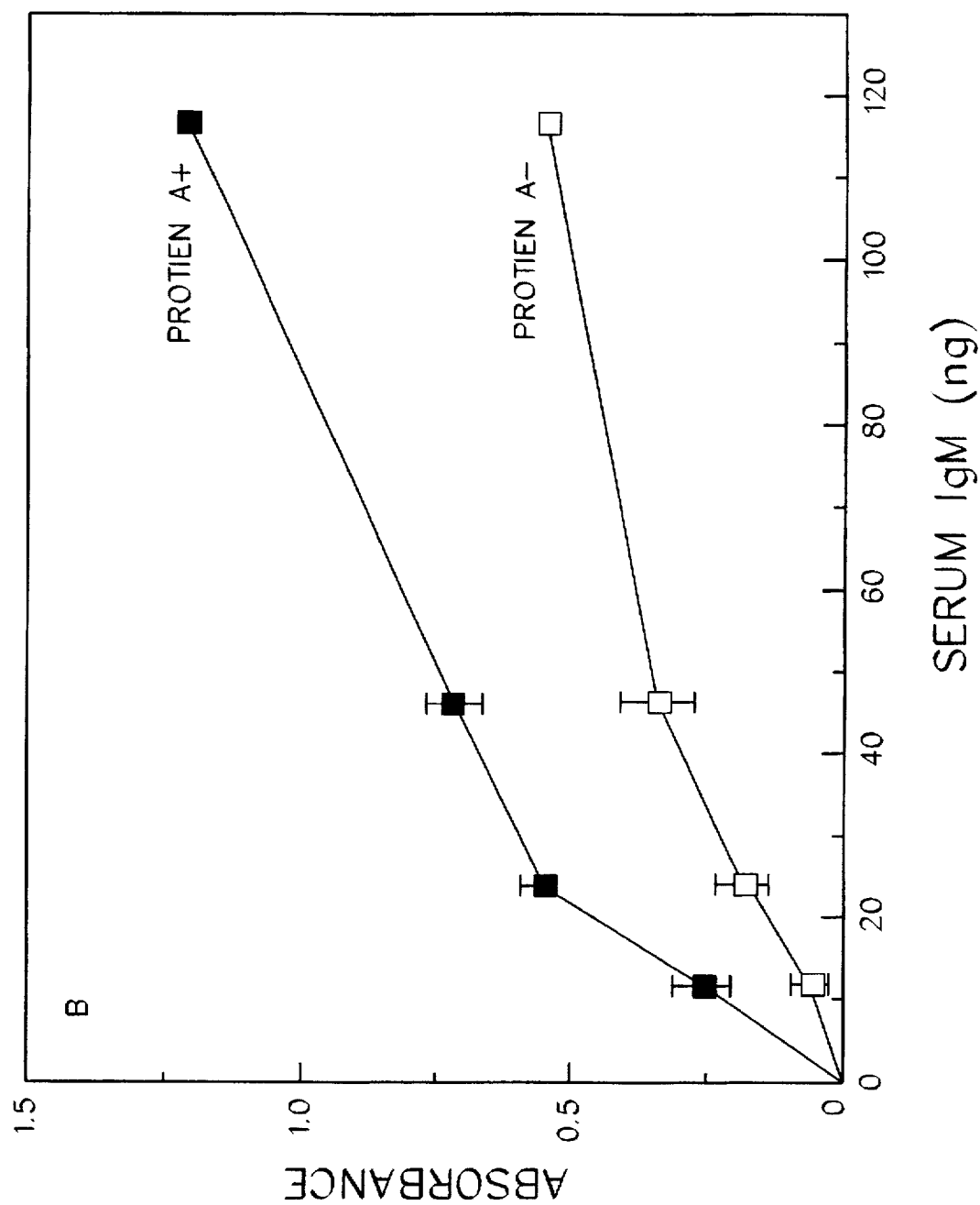

We discovered that the gp120 binding activity was enriched in the protein A-bound fraction (■) and depleted in the unbound fraction (□) as illustrated in FIG. 3B. Table 2 illustrates the result of an experiment wherein each fraction from the Protein A affinity column was titrated by ELISA for IgM binding to recombinant gp120 encoded by the indicated HIV strains. Values ($C_{50\%}$) are expressed as the IgM concentration in nanograms yielding an OD of 0.5 (midpoint of the titratable assay range).

The increased activity of the protein A-bound fraction was consistent for gp120 from different HIV strains and was unrelated to the recombinant protein expression system (Table 2). In addition, binding of both glycosylated and nonglycosylated gp120 indicated that the recognized epitope was peptide encoded.

TABLE 2

Binding of IgM to gp120 derived from different HIV strains

| HIV strain | C50 (ng) | |
|---|---|---|
| | Protein A+ | Protein A− |
| SF2 | 20.0 | >110 |
| SF2, non-glycos. | 42 | >110 |
| Δ IIIB | 13.5 | 41.5 |
| JRFL | 13.5 | >110 |
| JR-CSF | 32.0 | 84 |
| ST | 32.0 | >110 |
| Ba-L | 26.0 | 66 |

To examine whether a monoclonal population of IgM would bind to gp120, we evaluated a set of 14 monoclonal IgM paraproteins purified from sera of patients with Waldenstrom's macroglobulinemia (O. Axelrod et al., *Blood* 77:1484 (1991); T. Martin, S. F. Duffy, D. A. Carson, and T. J. Kipps, *J. Exp. Med.* 175:983 (1992)). Waldenstrom's macroglobulinemia is characterized by a diffuse infiltrate throughout the bone marrow of plasma cells, plasmacytoid lymphocytes, and lymphocytes, all of which were derived from a single B cell clone. This single B cell clone usually synthesizes IgM, and only rarely produces IgG or IgA.

Example 6 describes the method used to quantitate the interaction between gp120 and human paraproteins.

EXAMPLE 6

Paraprotein Binding to gp120

Purified paraproteins were isolated and V-gene characterized by Dr. Thomas Kipps. Paraprotein binding to gp120 or protein A was determined by direct ELISA using standard methods.

Figure 3C:
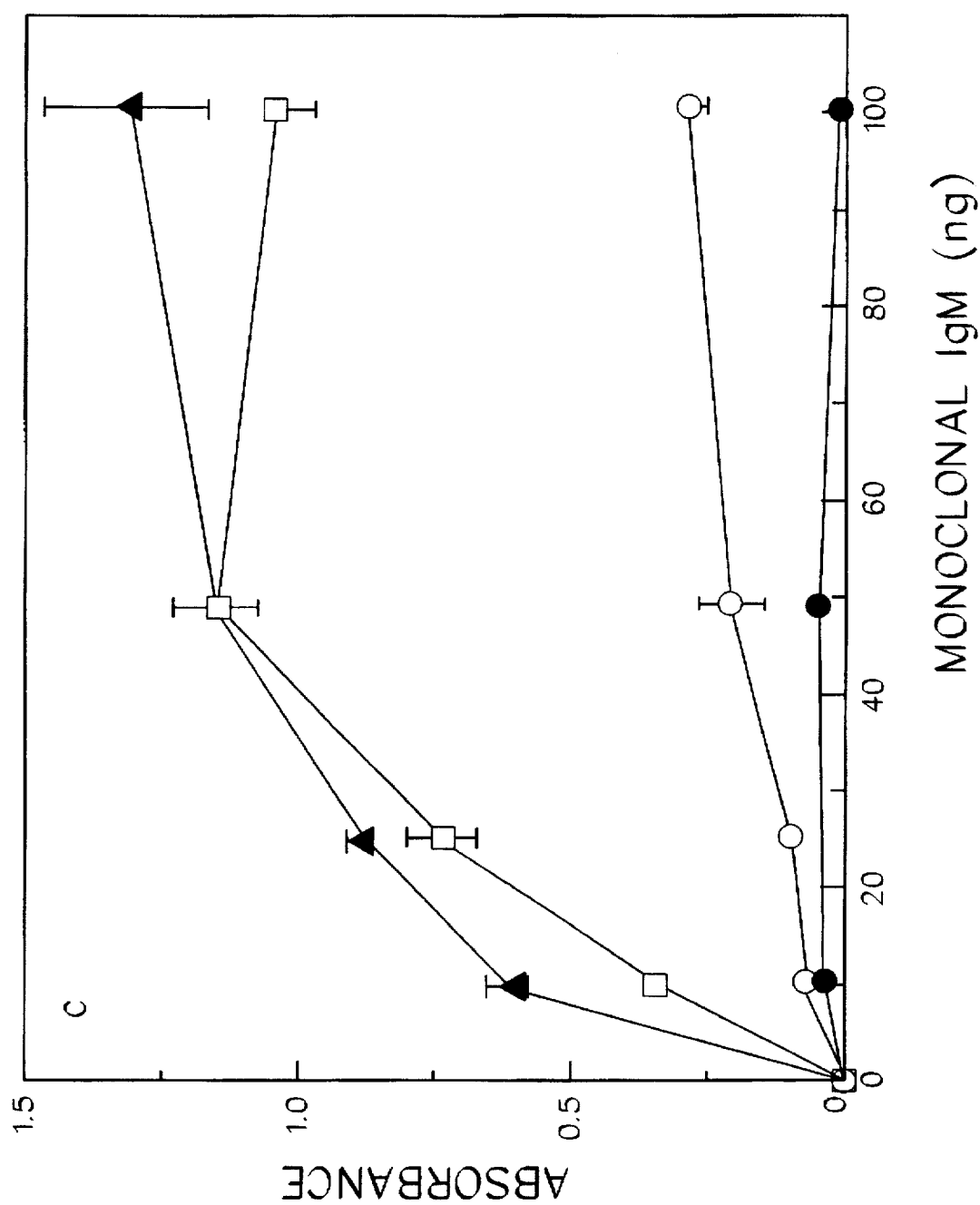

The results of these binding experiments are shown in FIG. 3C. In this figure, the samples were analyzed for absorbance at 492nm. A higher absorbance corresponds to a greater avidity.

Two IgM paraproteins, HEA (□) and A0103 (■), bound gp120 with a dose-dependence similar to serum IgM, and corresponded to the paraproteins which also avidly bound protein A (data not shown). In contrast, FIG. 3C illustrates that the IgM paraproteins SMI (●) and RJ293 (○) did not bind gp120, nor protein A (data not shown). It is unlikely therefore that multireactivity per se, as discussed above, accounts for gp120-binding, since SMI, a monoclonal IgM with typical multireactivity, lacks detectable gp120-binding activity.

Of the three paraproteins which bound to gp120 and Protein A, one was VH3 and two were VH4 (Table 3). We also found 11 paraproteins (two VH1, five VH3, two VH4, and two unclassified) which lacked binding activity (Table 3).

TABLE 3

Waldenstrom's Macroglobulinemia paraproteins and gp120-binding

| Paraprotein | VH | VL | Protein A | gp120 |
|---|---|---|---|---|
| A0103 | VH4 | Vk2 | positive | positive |
| JB043 | VH4 | Vk4 | positive | positive |
| HEA | VH3 | Vk3 | positive | positive |
| MAR | VH1 | Vk1 | positive | marginal |
| VIN | VH3 | Vk3 | positive | marginal |
| JB043 | VH4 | Vl | positive | marginal |
| IC461 | ND | ND | positive | marginal |
| SMI | VH1 | Vk3 | negative | negative |
| A0701 | VH4 | Vk4 | negative | negative |
| WH951 | VH3 | Vk1 | negative | negative |
| RJ293 | VH3 | Vl | negative | negative |
| KD477 | VH3 | Vk2 | negative | negative |
| A4053 | VH4 | Vk3 | negative | negative |
| EF985 | ND | ND | negative | negative |

Positive, $C_{50} < 20$ ng; marginal, 20 ng $< C_{50} < 100$ ng; negative, $C_{50} > 100$ ng.
ND, not determined.

The positive paraproteins and normal serum IgM were also distinguished from negative paraproteins by multireactivity, since they reacted with a limited but structurally diverse set of protein antigens (Table 4). We believe that the occurrence of binding activity in some VH4 paraproteins reflects the preferential utilization of VH4 gene products by this class of B-cell neoplasm, and the reported protein A-binding activity of a VH4 subset in normal serum Ig (E. H. Sasso, G. J. Silverman, and M. Mannik, *J. Immunol.* 143:2778 (1989); E. H. Sasso, G. J. Silverman, and M. Mannik, *J. Immunol* 147:1877 (1991)).

The findings illustrated in Table 4 indicated that VH3 binding to gp120 defined a new multireactive Ig family characterized by its unusual and unique antigenobinding profile.

TABLE 4

Multireactivity of gp120+ IgM

INSECT EXPRESSION PRODUCTS

+ gp120 IIIB
+ gp120 JRFL
+ bcr-abl (non-glycosylated nucleoprotein)
+ Bride of Sevenless (membrane glycoprotein)
MAMMALIAN EXPRESSION PRODUCTS + gp120 IIIB (recombinant CHO product)
+ BSA (Sigma)
− mouse Ig (several different monoclonal antibodies)
BACTERIAL EXPRESSION PRODUCTS + protein A
− protein G (tested by column binding, not ELISA)
− GST-VDJ (VH5) (VDJ-glutathione transferase fusion protein)
− GST-VDJ (VH3)
POLYSTYRENE PLATE − untreated
− treated with coating solution alone Summary of gp120-binding paraproteins and normal serum IgM, assayed by direct ELISA with the listed antigens.
(+) positive binding (−) negative binding To measure the binding affinity of gp120 and VH3 IgM, monoclonal VH3 IgM HEA was assayed by the method of Friguet et al. (B. Friguet, A. F. Chaffotte, L. Djavadi- Ohaniance, and M. E. Goldberg, *J. Immunol. Methods* 77: 305 (1985)), the disclosure of which is hereby incorporated by reference, in a liquid-phase competition binding assay with glycosylated $HIV_{SF2}$ gp120 as explained below.

Example 7 describes the method used to measure the affinity between gp120 and VH3 IgM.

EXAMPLE 7

Competition Binding Assay of gp120 and VH3

Briefly, gp120 at different concentrations was equilibrated in solution with fixed VH3 antibody concentrations. The mixture was introduced into antigen-coated ELISA plate wells, and the levels of plate-bound antibody (free) and plate-unbound (solution antigen-bound) were determined and analyzed by Scatchard analysis.

This experiment yielded a $K_D$ of 8.6 nM. Since this gp120 preparation was a highly pure, native conformation product (CHIRON, Emeryville, Calif.; lot MGC022; >90% by SDS-PAGE gel scan, 100% binding to soluble CD4), the high-avidity competition indicated that this VH3 IgM binds to gp120 in its native conformation. In this context, binding to nonglycosylated gp120 suggests two additional areas of progress pertinent to the application.

We were aware of the need to isolate representative anti-gp120 VH3 B-cell clones from normal B-cell populations. Previously, we had established panels of human hybridoma and EBV cell lines, by standard methods, from normal tonsil specimens enriched for VH3 B-cells. Using these panels, we screened culture supernatants from 71 cell lines (51 human hybridomas and 20 EBV cell lines) for the presence of the anti-gp120 antibody. Six of the 71 cell lines were positive, all expressing IgM (Table 5), and all were positive for the B6 idiotype (indicating use of a 56p1-like VH3 gene). This provided us with monoclonal antibodies and Ig gene sources for representative VH3/anti-gp120 IgM. The EBV cell line BOB-6, having the highest affinity for gp120, was deposited with the American Type Culture Collection (ATCC) on Jan. 20, 1993 as Accession Number CRL11242.

TABLE 5

Isolation of anti-gp120 B-cell lines derived from normal tonsil

|  | IgM | IgG |
|---|---|---|
| 65 cell lines | 25* | 27# |
| hybridoma 5 | 608 | 51 |
| hybridoma 11 | 409 | 9 |
| EBV1 | 354 | 9 |
| EBV2 | 268 | 22 |
| EBV5 | 467 | 32 |
| BOB-6 | 1260 | 15 |

Values are absorbance (OD × 10³) for undiluted supernatants assayed using peroxidase anti-IgM or anti-IgG. *range = 5–70; # values for 7 negative supernatants, range = 0–40.

Our finding that VH3 antibodies specifically interacted with gp120 led us to investigate whether the infection of target cells with HIV could be blocked by a competitive interaction between gp120 and the VH3 antibodies.

Example 8 illustrates the method used to demonstrate that VH3 antibodies could inhibit infection of target cells with HIV.

EXAMPLE 8

In vitro Inhibition of HIV Using VH3 Antibodies

HIV-1 JRFL viral supernatants (p24=125 ng/ml) were incubated at 4° C. for 30 minutes with either antibodies SMI, A0103, or human serum VH3 IgM. Antibody SMI does not bind gp120 whereas A0103 has positive gp120 binding characteristics. The VH3 IgM had been purified by sequential affinity chromatography using protein G depletion and protein A enrichment.

IL-2 stimulated PBL cells were then cultured with the treated viral supernatant for 3 hours at 37° C. without polybrene. The cells were then washed and cultured for 7 days followed by an assay for p24 (COULTER ELECTRONICS, Hialeah, Fla.). Since the VH3 homologue antibodies are the predominant V gene family in bovine serum, all phases of the experiment were performed in serum-free medium (AIM V, Bethesda Research Laboratory).

Figure 4A:
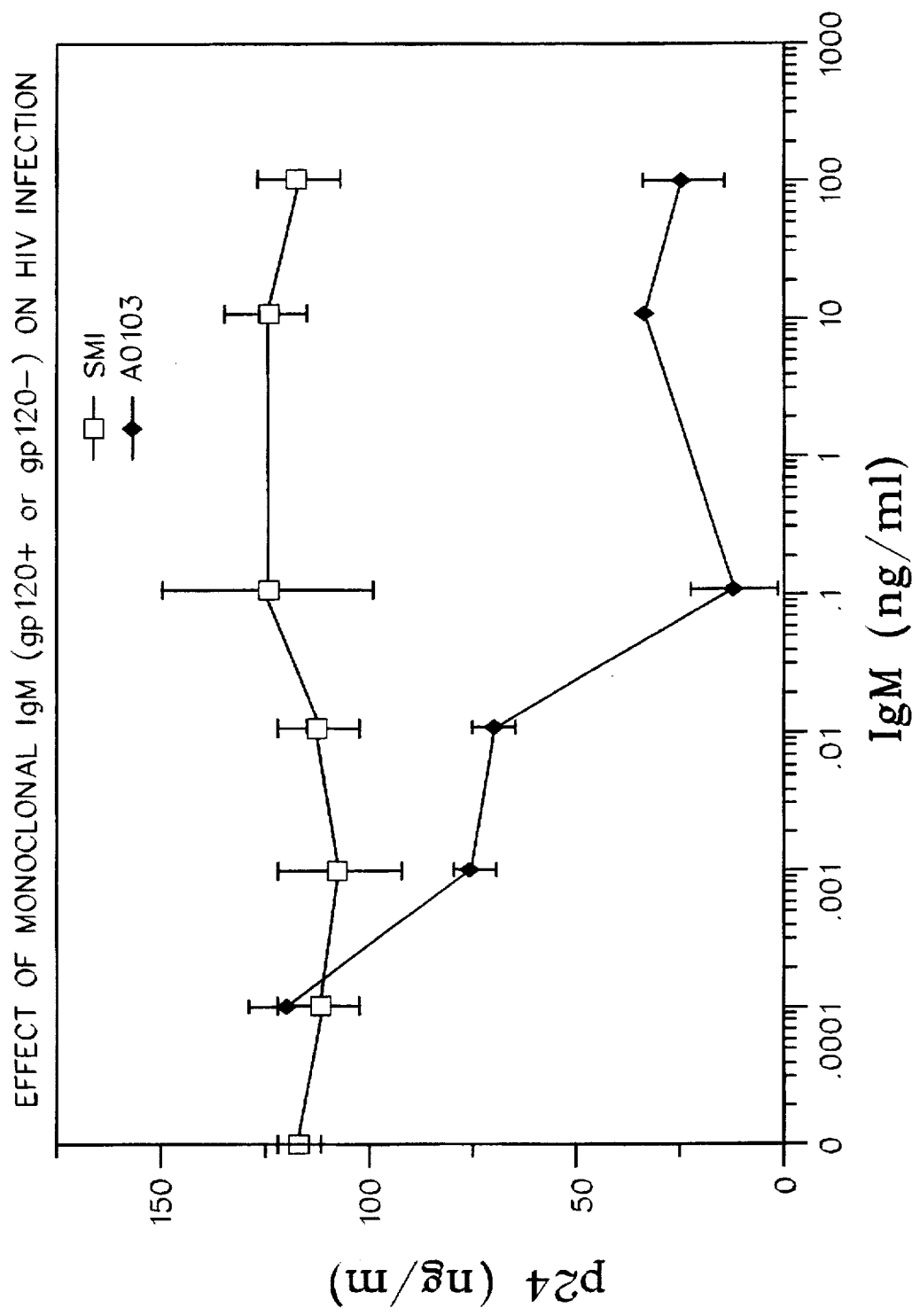
Figure 4B:
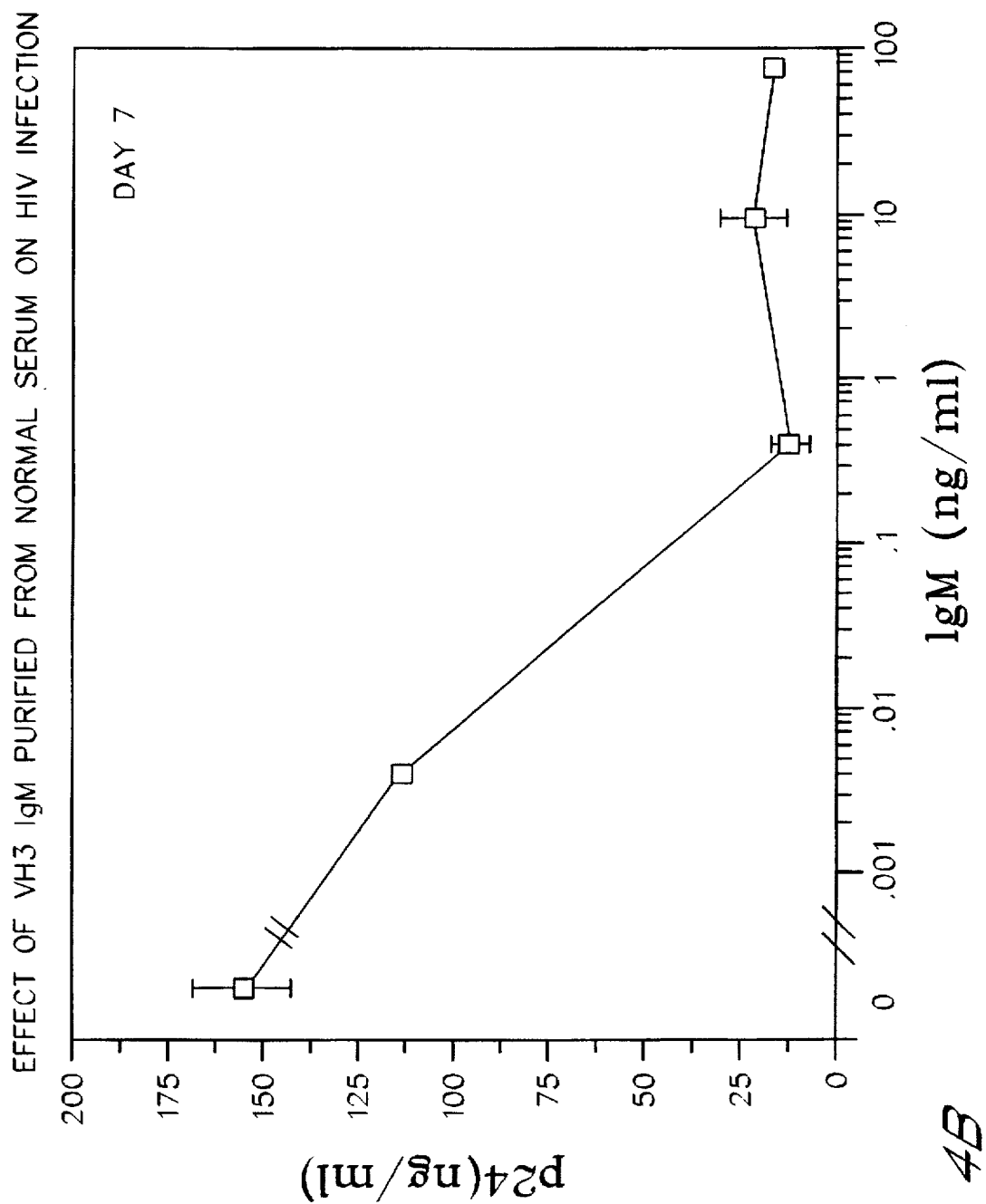

Under these conditions, the gp120- monoclonal antibody SMI (□) had little effect on HIV infection (FIG. 4A). However, the gp120+ A0103 (♦) antibody revealed a dose dependent inhibition of HIV infection. In addition, the VH3-enriched IgM from normal human serum dramatically reduced HIV infection as measured by p24 concentration in the supernatant (FIG. 4B). VH3 IgM provided a concentration dependent inhibition of p24. These findings show that both VH3 IgM (from serum) and VH4 IgM (from A0103) can have a potent neutralizing effect on HIV infection.

In light of the results obtained in these in vitro assays, we were interested in determining if there was a correlation between the amount of VH3 IgM antibodies and the progress of HIV disease state. In such an analysis, AIDS represents the most advanced disease state, ARC is less advanced, and asymptomatic status represents the least advanced disease state.

Example 9 illustrates the clinical relevance of VH3 IgM antibodies. In these procedures we measured the levels of IgM antibodies that were composed of VH3 gene products, or that expressed gp120 binding activity, or total HIV lysate antigens.

EXAMPLE 9

Correlation of VH3 Levels and HIV Disease State

Serum samples were obtained from each of 24 individuals who were evenly divided into 3 groups of 8 members each. The 3 groups were: (1) asymptomatic individuals, (2) individuals beset with AIDS-related complex (ARC), or (3) individuals with AIDS. The serum samples for each of the 3 groups were assayed for the presence of VH3 IgM antibodies. Each group was distinguished by the extent of blood CD4 T-cell depletion and clinical immunodeficiency.

An ELISA plate was coated with 50ng of recombinant gp120. Sera from each individual was diluted 1:50 in PBS/Tween and incubated in the coated ELISA plate. Goat anti-human IgM and peroxidase were added in a 1:1000 dilution to illuminate the bound sera-derived anti-gp120 antibodies.

The results shown in FIG. 5A demonstrate that all three parameters were statistically correlated with clinical stage of disease. Individuals that were asymptomatic had the highest titre of anti-gp120, followed by ARC individuals, and then finally individuals showing the full symptoms of AIDS who showed the lowest level of anti-gp120 antibodies. The following student's t test values were determined:

| Normal Serum vs Asymptomatic | p = .15 |
| Normal Serum vs ARC Individuals | p = .0008 |
| Normal Serum vs AIDS Individuals | p = .0001 |
| Asymptomatic vs ARC Individuals | p = .1272 |
| Asymptomatic vs AIDS Individuals | p = .0076 |
| ARC Individuals vs AIDS Individuals | p = .07 |

In a related experiment, the anti-VH3 paraprotein B6 was used to identify gp120 binding antibodies that were members of the VH3 gene family. An ELISA plate was coated with 50ng of gp120, sera from each individual was diluted 1:50 in PBS/Tween and incubated on the ELISA plate. A 1:500 dilution of the B6 antibody was added to the plates, followed by a 1:1000 dilution of goat anti-mouse IgG peroxidase. The anti-mouse IgG illuminated those gp120 antibodies in the serum that bound B6. The results of this experiment are shown in FIG. 5B. Patients in the AIDS and ARC groups had lower titers of VH3 IgG than those in the normal group. The statistical significance of this experiment was determined by the student's t test as shown below.

| Normal Serum vs Asymptomatic | p = .6 |
| Normal Serum vs ARC Individuals | p = .7 |
| Normal Serum vs AIDS Individuals | p = .02 |
| Asymptomatic vs ARC Individuals | p = .97 |
| Asymptomatic vs AIDS Individuals | p = .03 |
| ARC Individuals vs AIDS Individuals | p = .03 |

This data shows that the level of advancement of HIV disease state is well correlated with the level of antibodies with superantigen binding to gp120.

Since IgM antibodies composed of VH3 gene products had the lowest titre in individuals with full AIDS symptoms, we reasoned that B cells expressing VH3 genes might also be reduced in HIV-infected patients.

Example 10 illustrates the procedure used to assess state of the VH3 B cell population in individuals who were either HIV negative, HIV positive (without clinical onset of AIDS), or AIDS positive.

EXAMPLE 10

In Vivo Response of B cells to HIV Infection

Blood mononuclear cells were obtained from subjects enrolled in the Multicenter AIDS Cohort Study, a prospective study of the natural history of HIV infection. Samples from 45 patients were analyzed for CD19 and D12 idiotopes using well-known anti-idiotypic antibodies and flow cytometry. CD19+ cells were classified as B cells, and D12+ cells were those B cells that expressed VH3 gene products. Results of this experiment are shown in FIG. 6. Values are expressed as the percentage of D 12+/CD19+ B cells (ie. %D12+B cells). On the horizontal axis of FIG. 6, Group 1 is HIV negative (heterosexual), Group 2 is HIV negative (homosexual), Group 3 is HIV positive (without clinical onset of AIDS), and Group 4 is AIDS positive.

The results of this experiment illustrate that D12+ B cells are elevated in the initial stages of HIV infection, as measured by seropositive individuals having no clinical onset of AIDS. The number of D12+ B cells drops markedly in patients with clinical AIDS. This suggests that VH3 B cells are initially activated to expand in response to HIV infection, but then are removed from circulation once the patient enters the clinical AIDS stage.

We also investigated the possibility that individuals who were classified as HIV seropositive "long term survivors" (LTS) would have high levels of circulating VH3 Ig. We reasoned that a correlation should exist between VH3 Ig levels and the clinical progression of HIV infection if VH3 Ig served a protective role.

Example 11 illustrates the positive correlation between LTS status and the concentration of serum VH3 Ig.

EXAMPLE 11

HIV Infected Long Term Survivors Have High Concentrations of Circulating VH3 Ig

Blood samples were obtained from subjects enrolled in the Multicenter AIDS Cohort Study. All samples were categorized as having been donated by individuals who were either HIV seronegative, HIV seropositive or HIV seropositive "long term survivors" (LTS). In this context, the LTS classification indicated individuals who had survived at least 8 years after seroconversion without clinical signs of immunological impairment. The LTS population represents approximately 5% of the total seropositive population.

We measured VH3 Ig levels in all serum samples according to the method described by Berberjan et al., in J. AIDS 7:641 (1994). Results of these measurements are presented in FIG. 7. Compared to the HIV seronegative controls, the LTS group had normal levels of circulating IgM and anti-gp120 IgM. Significantly, there was a selectively high level of VH3 Ig in the LTS group, that was most striking in the VH3 Ig having the superantigen binding site, "D12+anti-gp120."

These findings indicated that the LTS group was characterized by a selective increase in superantigen-binding VH3 Ig as compared with the more conventional anti-gp120 Ig. This finding correlated with the protected state and argued that the superantigen-binding VH3 antibody subset functioned as the protective element.

The foregoing results suggested that anti-gp120 IgM could be used to neutralize HIV infection. Example 12 describes some of the contemplated methods of obtaining and using anti-gp120 IgM to neutralize HIV infection.

EXAMPLE 12

Use of Natural Anti-gp120 IgM to Neutralize Infectivity of HIV

The preceding section provided both direct in vitro evidence that the natural anti-gp120 antibody neutralizes infectivity of HIV, and correlative evidence that loss of these antibodies associates with and thus may be causally related to in vivo CD4 T-cell depletion and immunodeficiency.

As indicated above, we have generated several hybridomas or EBV cell lines producing natural VH3 anti-gp120 IgM antibodies. The recombinant-derived products produced by isolation and expression of VH and VL gene segments from B-cell clones producing the VH3 class of antibodies used are within the scope of this invention. These recombinant products include but are not limited to transfectomas, transgenic milk protein, and procaryote immunoglobulin cloning and expression systems (eg., filamentous phage).

It should be noted that these monoclonal antibodies have unique advantages compared to previously described anti-HIV antibodies. Many previously described antibodies are highly strain-specific, and thus are of limited usefulness due to antigenic drift of virus in a single patient, or when the diverse strains in a population are considered. Efforts to produce more broadly reactive antibodies have resulted in molecules that are dependent on discontinuous epitopes and native protein conformation, while still retaining deficits in strain reactivity. In contrast, the antibodies of the present invention are more broadly strain-reactive. So far, all tested HIV strains, including gp120 from the distantly related HIV-2 virus (see Table 2, isolate Ba-L), have shown detectable cross-reactivity. These antibodies also react with denatured as well as native conformation gp120.

We believe that VH3 IgM is useful as an immunogen against HIV infection in vivo. One method of treating patients at risk or with an HIV infection is through passive immunotherapy.

Example 13A illustrates how passive immunotherapy can be used to provide protection against HIV infection.

EXAMPLE 13A

Passive Immunotherapy

The passive immunotherapy method can supplement or restore the naturally occurring levels of VH3 anti-gp120 IgM in individuals with HIV infection or at risk for infection. Passive immunotherapy by intravenous infusion of IgG-enriched immunoglobulin isolated from donor pools is a FDA-approved therapy for a variety of infectious and autoimmune diseases. In an exemplary protocol, a person is injected with 400mg/kg of VH3 IgG enriched immunoglobulin at 4 week intervals for an indefinite time period. These injections could be subcutaneously, intradermally, intravenously, intramuscularly, topically and intraperitoneally. We believe that injections of this type will reduce the amount of active HIV virus in the person. The antibody molecules for this method are derived from VH3 enriched serum, or hybridomas. Methods for enriching serum for gp120-binding are disclosed in the above examples. Fragments of the monoclonal antibodies used in this method are also anticipated. Although 400mg/kg is believed to be an appropriate anti-HIV dose, other dosages of VH3 enriched immunoglobulin are also anticipated. For instance, dosages between 50mg/kg and 4g/kg are believed effective. This method is specifically supported by the successful use of anti-HIV immunoglobulin to block HIV infection in the chimpanzee. However, in the chimpanzee experiments the immunoglobulin pools were not enriched for VH3. We believe that VH3-enriched immunoglobulin pools would be still more effective.

One assay for assessing the benefit of passive infusion would involve the use of passive immunotherapy to suppress HIV infection in SCID mice reconstituted with blood lymphocytes (by D. Mosier) or lymphold tissue (by J. McCune and SYSTEMIX Corporation, Palo Alto, Calif.).

Example 13B illustrates an assay for passive immunotherapy using a SCID mouse model.

EXAMPLE 13B

Assay of Passive Immunotherapy

The SCID mice can be injected intraperitoneally, intradermally, subcutaneously, intravenously, or any other method known to those with skill in the art with VH3 immunoglobulins after being reconstituted with human blood lymphocytes and infected with HIV. Following injection with VH3, the titre of HIV in the mice will diminish, indicating an inhibition of HIV.

In addition, we believe that restoration of natural VH3 anti-gp120 IgM levels in individuals with HIV may be beneficial for reasons distinct from HIV neutralization perse. It was noted previously that the VH3 class of antibodies is multireactive. It is believed by those with skill in the art that multireactive antibodies serve important roles in host-defense to infectious diseases, and maintaining a normal immunoregulatory environment. This point is of potential importance in slowing or correcting the proposed immunopathogenic processes in HIV infection. To prove this theory, passive immunotherapy can be performed in human trials with HIV-infected individuals. These individuals are passively immunized, as discussed above, and then monitored for objective immune function, episodes of infection, progression of disease, and/or survival. A decrease in episodes of infection and progression of the disease indicates that the multireactive VH3 antibodies are affecting the host-defense mechanism. Similarly, an increase in the individual survival length indicates a relation between the multireactive antibody and the host-defense system.

In addition to passive immunotherapy, we believe that active immunotherapy can be of value to individuals who are at risk for, or who have HIV. These active immunotherapy procedures are discussed below.

It has been well-established that immunization under appropriate conditions with immunoglobulin stimulates clonal expansion and increases production of serum antibody by B-cell clones expressing immunoglobulins structurally related to that used for immunization (Paul WE, Bona C, Regulatory idiotopes and immune networks a hypothesis. *Immunol. Today* 3:230–234 (1982)). We believe that immunization with natural anti-gp120 IgM or recombinant-derived equivalents can stimulate the corresponding B-cell clones of individuals with HIV infection or at risk for infection. In this manner, the person infected with HIV will be stimulated to produce their own VH3 IgM.

Example 14 illustrates an active immunotherapy protocol that could be used to stimulate an immune response that would be protective against HIV infection.

EXAMPLE 14

Active Immunotherapy

A group of individuals is injected with a solution containing anti-gp120 IgM (VH3). The anti-gp120 antibodies would then stimulate clonal expansion leading to an increased immune response against the HIV. In addition to using multireactive antibodies to treat HIV infection, other diseases are also believed treatable using these molecules. These diseases include other bacterial, viral and fungal infections.

Example 15 illustrates how multireactive immunoglobulins can be used to neutralize infection by other pathogens.

EXAMPLE 15

Use of Multireactive Immunoglobulins to Neutralize Infection by Other Pathogens IVIG therapy is of proven value for treatment of several infectious diseases. Multireactive IgM represents an alternate antibody subset that should be useful for this purpose, since these antibodies are broadly reactive against microbial pathogens, and are widely believed to serve a natural role in host defense against pathogens.

We believe that multireactive antibodies are related to the families of chaperone proteins. Chaperones are proteins with the property of binding to many structurally distinct proteins or peptides, and are important in biologic processes ranging from protein biosynthesis to cell recovery from cellular injury. Notably, there are several classes of chaperones, each of which shares a distinct pattern of avidity for various proteins and/or peptides.

Both our own observations and the available literature suggest that multireactive antibodies are divided into binding classes. For example, the SMI antibody discussed above in reference to FIG. 3C reacts with DNA and immunoglobulin Fc, but not HIV gp120, bcr-abl, or protein A; the converse was true of HEA, A0103, and JB043 (FIG. 3C). Due to the breadth of reactivity in each class, and by comparison to chaperones, it is unlikely that there are more than 2–4 multireactive antibody classes. A combination of single representative B-cell clones and their immunoglobulins (or recombinant equivalents) from each class is expected to serve the biologic role of the entire natural mix of multireactive B-cells and their products.

The scope of the present invention is also meant to include the use of multireactive immunoglobulins (including but not limited to those represented by the anti-gp120 VH3 IgM subset) in immunotherapy for microbial pathogens. This would include products, passive immunotherapy, and active immunotherapy as defined in the preceding section. It is expected that this therapy is useful not only for individuals with a selective clonal VH3 deficit, such as HIV infection and common variable immunodeficiency, but also for all patient groups currently approved for IVIG therapy. The clinical application of our discovery of multi-reactive antibodies against HIV represents a major improvement over existing IVIG therapy. We believe that a therapy based on the use of multi-reactive anti-HIV antibodies will be safer, more reliable, more potent and much less costly than conventional IVIG therapy.

To practice this method, a patient suffering from a pathogenic substance is injected with a composition mostly comprising multireactive immunoglobulins with an avidity for the pathogen. This injection can be intravenously, intramuscularly, intradermally, or any other method known to those with skill in the art. The injections would continue over a period of time until the pathogen was effectively removed from the body. We believe that injections within the range of approximately 50mg/kg to 4g/kg every two to eight weeks for an indefinite time period will provide an active therapy for this type of patient. Of course, injections of multireactive antibodies against the pathogen at different, pharmacologically active concentrations would also be within the scope of this invention.

In addition to treating pathogens with multireactive antibodies, we can also produce a murine model for HIV infection.

Example 16 describes a contemplated murine model for HIV infection that is intended to fall within the scope of the invention described herein.

EXAMPLE 16

A Murine Model for HIV Infection

The VH3 gene family is highly homologous between species. Thus, we believe that natural, anti-gp120 IgM B-cells and serum IgM exist in mice. However, the mouse does not propagate HIV infection in vivo. We believe that this is due to the infrequency of target lymphocytes. Murine CD4 is not a ligand for gp120, leaving only the low frequency of probable gp120-binding B-cells. This frequency is presumably only approximately 4% B-cells, as in the human. A method of producing an HIV infection in mice can be based on infecting B-cells, instead of the previous methods of attempting to infect T-cells.

HIV infection of neonatal mice

Multireactive B-cells are much more abundant in neonatal mice than adults, representing approximately 50% of all B-cells. Based on the precedent of CD4 T cells in humans, we believe this frequency is sufficient to propagate HIV infection in murine populations. It is known that human B-cells can propagate HIV infection. We will use neonatal mice for in vivo HIV infection by intravenous or intraperitoneal HIV inoculation. Intravenous, intralymphoid, or intraperitoneal injections of virus will be given to the neonatal mice. Experience in the art demonstrates the effectiveness of this method of in vivo infection in mice bearing infectable target populations (J. M. McCune, *Immunol. Rev.* 124:45–62, (1991)). The neonates will propagate their infection in B-cells by the method discussed above. The utility of this infection system is as an animal model for investigation of therapies relevant to HIV infection and its complications. This includes, but is not limited to, vaccine development and anti-viral pharmaceuticals.

Human anti-gp120 VH3 IgM transgenic mice.

An alternate way to produce a large target population of murine cells for HIV infection is through transgenic mice using immunoglobulin genes from human B-cell clones, by the method described above. It is a well-established technology to produce immunoglobulin transgenic mice which express the transgene as membrane Ig on nearly all mature B-cells (B. Rogerson, et al., *EMBO J.* 10:4331–4341, (1991) ). Transgenic mice using human natural anti-g120 VH3 IgM genes can thereby be produced as a murine system for HIV infection, and its applications are as an animal model system for the study of HIV infection, its complications, and relevant therapies.

One method of using such a model system would be to determine effective treatments for combating HIV infection. A transgenic mouse is produced by the above method and intravenously injected with HIV. A period of time is allowed to pass so that an HIV infection develops in the mouse. The treatment in question is administered to the mouse by the most advantageous method. After allowing the treatment to become effective, the mouse is assayed for HIV infection. A reduction in the amount HIV infection indicates that the treatment was effective.

We have also developed a murine model system using the SCID-hu-PBL mouse. This experimental system can be used to facilitate the identification and development of HIV therapeutic agents based on superantigens.

Example 17 illustrates how our murine model system can be used to study the in vivo relevance of VH3 Ig in HIV infection.

EXAMPLE 17

HIV Infection in SCID-hu-PBL Mice Selectively Affects gp120-Specific Serum Ig

Reconstituted SCID-hu mice (10 per group) were either left as uninfected controls, or infected with the SF33 or SF162 strains of HIV–1. At 2 weeks post-infection the mice were bled to recover serum for ELISA quantitation of total IgM, D12 IgM, and anti-gp120 IgM levels. The results of this experiment are shown in FIG. 8. Means and SEM are normalized for IgM subset levels for the normal group. We found that the SF33 strain increased serum IgM levels, and the SF162 strain reduced serum IgM levels. In both cases, the predominate humoral immune response was gp120-specific IgM.

We have further modeled the B cell response to HIV infection in SCID-hu-PBL mice. In this system, propagation of viral infection of the engrafted human mononuclear cells was robust with a variety of HIV-1 strains. However, pathologic effects on CD4 T cell depletion were only elicited by a subset of viral strains (e.g., SF162 but not SF33). We therefore compared levels of serum IgM subsets in groups of mice two weeks after SF33, SF162 or mock infection. SF33 infection resulted in a general increase in serum IgM; while it appeared that VH3 (D12 idiotope) and anti-gp20 IgM were increased more than total IgM. In contrast, the pathogenic SF162 strain did not elicit a significant change in levels of total or D12 IgM 2-fold increase of serum IgM, and 8-fold increase in D12 and anti-gp120 IgM. Further, there was a striking and selective depletion of anti-gp120 IgM in these mice. The preferential loss of anti-gp120 IgM levels indicates that antigen-specific secretory B cells were selectively susceptible to this virus-induced response.

The foregoing description illustrates a mouse model that can be used to test the therapeutic potential of B cell superantigens. In particular, this murine model can be used to test the inhibition of HIV infection and its consequence on B and T cell activity.

In addition to the neutralizing role of anti-gp120 antibodies, there is also evidence that under some conditions such antibodies can enhance viral infection.

Example 18 illustrates how either passive or active immunotherapy can be used to block the enhancing role of natural anti-gp120 IgM.

EXAMPLE 18

Use of Passive or Active Therapy to Block Enhancing Role of Natural Anti-gp120 IgM In the presence of anti-gp120 antibodies, HIV is sequestered in an antibody-virus immune complex. In the case of IgG, this immune complex can be taken up by cells via the Fcg-receptor. In the case of both IgG and IgM, C3 peptide association with the immune complex allows a second mode of immune complex uptake via cellular C3 receptors.

We believe that HIV could rapidly form immune complexes in vivo, predominantly with normally-occurring VH3 IgM. These immune complexes are believed to be able to fix complement, and thus efficiently be taken up by the many types of cells which express complement receptors. Following virus uptake, these cells support the intracellular viral life-cycle and virus production, thereby propagating viral infection in the host. We therefore believe that HIV has evolved to use a common immunoglobulin V gene family as a major host receptor.

Example 19 illustrates a method that can be used to eliminate the B-cell clones that are the producers of antibodies that enhance viral infection.

EXAMPLE 19

Elimination of Enhancing Antibody-Producing Clones

The most direct method for eliminating enhancing serum antibodies is to immunologically inactivate or destroy the B cell clones of origin. A well-established method for this purpose is immunization of individuals with the clonal immunoglobulin, eliciting a clonally suppressire immune response through the action of anti-clone T ceils and anti-idiotypic antibodies (D. W. Brighty, M. Rosenberg, I. S. Y. Chen, and M. Ivey-Hoyle, *Proc. Natl. Acad. Sci.* 88:7802 (1991); M. Ivey-Hoyle et al., ibid 88:512 (1991 )). It is notable that precedents for successful clonal therapy are well-documented in human clinical studies (Brown S. L., Miller R. A., Homing S. J., Czerwinski D., Hart S. M., McElderry R., Basham T., Warnke R. A., Merigan T. C., Levy R., Treatment of B cell lymphoma with anti-idiotype antibodies alone and in combination with alpha interferon. *Blood* 73:651–661 (1989)). We have already produced antibodies characteristic of these clones that can be used for active immunotherapy. We also have produced murine anti-clone antibodies that can be used for passive immunotherapy.

The foregoing results confirmed that the gp120 envelope glycoprotein of HIV-1 functioned as an Ig-SAg. Classification of gp120 as an Ig-SAg was based on the following criteria: (i) gp120 binds to an inordinately large population (4–6%) of endogenous B cells via their membrane Ig, (ii) gp120 binds to a variety of preimmune Ig VH regions, the majority, if not all, are members of the VH3 family, (iii) gp120 stimulates B cells (obtained from HIV seronegative individuals) in culture to secrete VH3 Ig, and (iv) clinical HIV-1 infection correlates with a selective activation and eventual depletion of gp120-binding VH3 B cells.

These findings led us to explore the possibility that a single continuous peptide motif in gp120 was responsible for the endogenous Ig binding activity detailed above. This investigation employed a conventional competition binding assay utilizing 31 gp160 peptides; 29 of these peptides were from gp120. These peptides were preincubated with polyclonal serum IgM to allow it to occupy the Ig-SAg binding site. This mixture was then added to gp120-coated microtiter wells and the residual binding capacity of the antibody to the immobilized gp120 was measured.

Example 20 describes the procedure used to investigate the nature of the interaction between gp120 and IgM that accounted for superantigen activity.

EXAMPLE 20

A Peptide Competition Assay Used to Detect Interactions Between gp120 and Endogenous Serum IgM A set of 31 peptides was obtained from the AIDS Research and Reference Reagent Program, NIH. The sequences and origins of these peptides are presented in Table 6. All peptides used in these procedures were 16–34 amino acids in length, and were synthesized from the sequences of gp120 or gp41 from HIV-1 strains MN, HXB2, IIIB, Z3, or CDC42. The peptides were dissolved at a concentration of 1 mM in the solvent recommended by the supplier unless stated otherwise. Peptides #1919, 1922, 1925, 1959, 1960, 1987, 1988, 1989, 2007, 2008, 2012, 2013, 2015, 2021, and 2022 were dissolved in 0.01% trifluoroacetic acid (TFA). TFA alone at doses of <0.1% did not inhibit the binding of peptides to Ig or the binding of Ig to gp120. Peptides #1923, 1929, and 1934 were dissolved in the minimal required amount of acetic acid (8.8%, 6.0%, and 5.3% acetic acid, respectively). However, when peptides #1923, 1929, and 1934 were used at a final concentration of ≧10 μM, the acetic acid solvent inhibited Ig binding. Therefore, these three peptides were only used at concentrations <10 μM. All peptides were stored at −80° C.

TABLE 6

HIV-1 gp 160 peptide sequences

| PEPTIDE | AMINO ACIDS | SEQUENCE | SEQ ID NO: | HIV STRAIN |
|---|---|---|---|---|
| 1919 | 1–20 | MRVKGIRRNYQHWWGWGTM | (SEQ ID NO: 1) | HIV-1 MN |
| 1922 | 31–50 | EKLWVTVYYGVPVWKEATTT | (SEQ ID ND: 2) | HIV-1 MN |
| 1923 | 41–60 | VPVWKEATTTLFCASDAKAY | (SEQ ID NO: 3) | HIV-1 MN |
| 1929 | 101–120 | EQMHEDIISLWDQSLKPCVK | (SEQ ID ND: 4) | HIV-1 MN |
| 1925 | 61–81 | DTEVHNVWATQACVPTDPNP | (SEQ ID ND: 5) | HIV-1 MN |
| 1934 | 151–170 | EGTIKGGEMKNCSFNITTSI | (SEQ ID ND: 6) | HIV-1 MN |
| 747 | 200–217 | VITQACPKVSFEPIPIHY | (SEQ ID NO: 7) | HIV-1 MN |
| 748 | 21D–227 | FEPIPIHYCAPAGFAILK | (SEQ ID NO: 8) | HIV-1 HXB2 |
| 749 | 223–238 | CAPAGFAILKCNDKKF | (SEQ ID ND: 9) | HIV-1 MN |
| 743 | 228–246 | CNNKTFNGTGPCTNVSTVQ | (SEQ ID ND: 10) | HIV-1 HXB2 |
| 1959 | 231–250 | LKCNDKKFSGKGSCKNVSTV | (SEQ ID ND: 11) | HIV-1 MN |
| 1960 | 241–260 | KGSCKNVSTVQCTHGIRPVV | (SEQ ID NO: 12) | HIV-1 MN |
| 746 | 238–254 | TGPCTNVSTVQCTHGIRPV | (SEQ ID ND: 13) | HIV-1 HX82 |
| 1590 | 295–321 | TRPNNNTRKSIRIQRGPGRAFVITGKIGNMRQAH | (SEQ ID NO: 14) | HIV-1 HXB2 |
| 1985 | 301–320 | CTRPNYNKRKRIHIGPGRAF | (SEQ ID ND: 15) | HIV-1 MN |
| 864 | 306–327 | YNKRKRIHIQRGPGRAFYTTKNII | (SEQ ID NO: 16) | HIV IIIB + MN |
| 1987 | 321–340 | YTTKNIIGTIRQAHCNISRA | (SEQ ID NO: 17) | HIV-1 MN |
| 1988 | 331–350 | RQAHCNISRAKWNDTLRQIV | (SEQ ID ND: 18) | HIV-1 MN |
| 1989 | 341–360 | KWNDTLRQIVSKLKEQFKNK | (SEQ ID ND: 19) | HIV-1 MN |
| 1587 | 350–378 | REQFGNNKTIIFKQSSGGDPEIVTHSFNC | (SEQ ID ND: 20) | HIV-1 IIIB |
| 1990 | 351–370 | SKLKEQFKNKTIVFNQSSGG | (SEQ ID NQ: 21) | HIV-1 MN |
| 702 | 405–423 | TGNITLPCRIKQVVRTWQG | (SEQ ID ND: 22) | HIV-1 Z3 |
| 2007 | 421–440 | KQIINMWQEVGKAMYAPPIE | (SEQ ID NC: 23) | HIV-1 MN |
| 1589 | 418–441 | CRIKQIIMWQKVGKAMYAPPISG | (SEQ ID ND: 24) | HIV-1 IIIB |
| 703 | 419–438 | TGDIITLPCRIKQIINRWQV | (SEQ ID ND: 25) | HIV-1 CDC42 |
| 2008 | 431–450 | GKAMYAPPIEGQIRCSSNIT | (SEQ ID ND: 26) | HIV-1 MN |
| 2012 | 471–490 | RPGGGDMRDNWRSELYKYKV | (SEQ ID NO: 27) | HIV-1 MN |
| 2013 | 481–500 | WRSELYKYKVVTIEPLGVAP | (SEQ ID ND: 28) | HIV-1 MN |
| 2015 | 501–520 | TKAKRRVVQREKRAAIGALP | (SEQ ID ND: 29) | HIV-1 MN |
| 2021 | 561–580 | EAQQHMLQLTVWGIKQLQAR | (SEQ ID ND: 30) | HIV-1 MN |
| 2022 | 571–590 | VWGILQLQARVLAVERYLKD | (SEQ ID ND: 31) | HIV-1 MN |

Microtiter plates (Costar, Cambridge, Mass.) were coated overnight (4° C.) with 50 ng/well of recombinant of gp120 from HIV-1$_{SF2}$ (expressed in Chinese hamster ovary cells, a gift from Kathelyn Steimer, Chiron Corporation). The recombinant gp120 was diluted in carbonate-bicarbonate buffer, pH 9.6 (Sigma, St. Louis, Mo.). The plates were rinsed 3×with PBS made 0.5% Tween-20, and blocked for 15 minutes at room temperature with the same solution.

Normal human polyclonal IgM was also obtained from Sigma. It should be noted that similar results were obtained using either whole serum or IgG-depleted serum. All serum samples were from HIV seronegative individuals.

Samples of IgM (diluted in PBS made 0.5% Tween-20) were preincubated at 4° C. for 15 hours with various concentrations of peptides in microfuge tubes. This IgM/peptide solution was added to the gp120-coated plates and incubated for 1 hour at room temperature. The polyclonal serum IgM employed in these procedures was used at a final concentration of 1 µg/ml. After washing (3×with PBS made 0.5% Tween-20), wells were incubated for 1 hour at 4° C. with goat anti-human IgM-horseradish peroxidase (Southern Biotechnology Associates, Birmingham, Ala.), washed, and reacted with 50 µl of o-phenylenediamine (OPD) dihydrochloride substrate (Sigma) for 10–20 minutes at 37° C. The colorimetric enzyme reaction was stopped by addition of 50 µl of 3 N $H_2SO_4$. Optical absorbances for all samples were determined at 492 nm using an ELISA reader with data-reduction software from Bio-Rad (Richmond, Calif.). All values were expressed as percent absorbance for each Ig in the absence of competing peptide. Peptides were scored as inhibitors of IgM binding to gp120 if they inhibited >50% at 1 or 10 µM.

The results from a representative experiment utilizing 19 gp 160 peptides derived from the MN strain of HIV–1 are shown in FIG. 9A. Seven of the peptides strongly inhibited the binding of serum IgM to gp120. This data is summarized in Table 7. Surprisingly, the inhibitory peptides corresponded to various sites in the gp120 envelope glycoprotein. These peptides were from each of the more conserved regions of gp120: C1, C2, C3, C4 and C5. The two pairs of inhibitory peptides from C2 and C3 were overlapping.

TABLE 7

Peptides which inhibit the binding of human IgM to gp 120

| | | | | RESIDUAL BINDING TO gp120 (% OF CONTROL) | |
|---|---|---|---|---|---|
| ANTIBODY | PEPTIDE # | AMINO ACIDS | gp120 DOMAIN | 1.0 µM PEPTIDE | 10.0 µM PEPTIDE |
| SERUM IgM: | 1919 | 1–20 | C1 | 17.6 ± 0.2 | ND |
| | 1959 | 231–250 | C2 | 37.0 ± 4.4 | 16.8 ± 8.4 |
| | 1960 | 241–260 | C2 | 19.2 ± 1.0 | 11.7 ± 2.3 |
| | 1988 | 331–350 | C3 | 39.9 ± 3.6 | 23.7 ± 9.7 |

TABLE 7-continued

Peptides which inhibit the binding of human IgM to gp 120

| ANTIBODY | PEPTIDE # | AMINO ACIDS | gp120 DOMAIN | RESIDUAL BINDING TO gp120 (% OF CONTROL) | |
|---|---|---|---|---|---|
| | | | | 1.0 µM PEPTIDE | 10.0 µM PEPTIDE |
| | 1989 | 341-360 | C3 | 88.5 ± 3.6 | 24.6 ± 6.6 |
| | 2007 | 421-440 | C4 | 59.1 ± 0.8 | 19.8 ± 5.4 |
| | 2015 | 501-520 | C5-gp41 | 44.5 ± 5.4 | 29.3 ± 5.1 |
| HEA: | 1919 | 1-20 | C1 | 56.1 ± 3.6 | 15.1 ± 2.1 |
| | 1959 | 231-250 | C2 | 28.3 ± 3.7 | 8.4 ± 5.3 |
| | 1960 | 241-260 | C2 | 11.3 ± 2.5 | 6.2 ± 3.0 |
| | 1988 | 331-350 | C3 | 92.8 ± 0.4 | 40.8 ± 6.1 |
| | 1989 | 341-360 | C3 | 98.3 ± 0.1 | 26.2 ± 0.8 |
| | 2007 | 421-440 | C4 | 56.2 ± 4.7 | 10.3 ± 0.5 |
| VIN: | 1919 | 1-20 | C1 | 28.1 ± 5.0 | 14.8 ± 2.0 |
| | 1959 | 231-250 | C2 | 12.6 ± 1.0 | 8.0 ± 0.2 |
| | 1960 | 241-260 | C2 | 6.2 ± 1.3 | 5.8 ± 1.3 |
| | 1988 | 331-350 | C3 | 12.4 ± 0.6 | 12.2 ± 7.8 |
| | 1989 | 341-360 | C3 | 96.6 ± 6.1 | 13.4 ± 1.8 |
| | 2007 | 421-440 | C4 | 69.8 ± 4.2 | 21.2 ± 1.2 |
| | 2008 | 431-450 | C4 | 108 ± 4.3 | 15.7 ± 1.7 |
| | 2015 | 501-520 | C5-gp41 | 23.7 ± 3.4 | 6.5 ± 2.0 |
| RSJ: | 1919 | 1-20 | C1 | 11.1 ± 1.5 | 1.3 ± 0.1 |
| | 1934 | 151-170 | V1-V2 | 13.9 ± 0.3 | ND |
| | 1959 | 231-250 | C2 | 40.5 ± 8.2 | 17.2 ± 1.7 |
| | 1960 | 241-260 | C2 | 10.2 ± 2.4 | 4.2 ± 5.0 |
| | 1987 | 321-340 | V3-C3 | 56.8 ± 0.3 | 42.2 ± 3.4 |
| | 1988 | 331-350 | C3 | 20.3 ± 1.5 | 13.5 ± 0.4 |
| | 2007 | 421-440 | C4 | 24.1 ± 0.1 | 3.1 ± 0.7 |
| VNG: | 1919 | 1-20 | C1 | 46.4 ± 20.2 | 3.3 ± 1.7 |
| | 1959 | 231-250 | C2 | 48.7 ± 0.9 | 13.7 ± 3.6 |
| | 1960 | 241-260 | C2 | 58.1 ± 0 | 32.3 ± 7.1 |
| | 1985 | 301-320 | V3 | 27.4 ± 0.5 | 24.2 ± 0.1 |
| | 2015 | 501-520 | C5-gp41 | 83.0 ± 6.3 | 37.7 ± 2.0 |

The fact that individual peptides could completely inhibit the gp120-IgM interaction had two implications. First, the endogenous IgM recognized a linear, peptide-encoded, non-glycosylated epitope. This point was confirmed by the fact that polyclonal serum IgM and 4 gp120-binding monoclonal IgM bound with an equal avidity to native gp120 and to a linear, nonglycosylated form of the molecule, env2-3 gp120 (L.G. and J.B., unpublished data). Second, since single peptides inhibited the binding of a diverse population of antibodies present in normal serum IgM, the binding sites of these antibodies share the same epitope specificity.

A panel of 29 monoclonal antibodies was next used to determine the fine specificity of binding of gp120 for an individual IgM. These monoclonal antibodies were identified from a random set of human monoclonal IgM obtained from patients with secretory B cell neoplasia. All patients were negative for HIV infection. Based on the findings presented below, a panel of four monoclonal IgM was selected as representing independent examples of antibodies with gp120 Ig-SAg binding activity.

Example 21 demonstrates the method used to identify the portion of the gp120 protein sequence that interacted with human monoclonal IgM.

EXAMPLE 21

Binding of Monoclonal IgM to gp120 is Inhibited by Shared and Unique Peptides

The direct binding ELISA assay described by Berberian et al., in *Science* 61:1588 (1993), and Berberian et al., in *J. AIDS* 7:641 (1994), was first used to assess the monoclonal IgM-gp120 interaction. Peptide competition assays were subsequently performed.

FIG. 10 presents the results of a direct binding assay which shows that, among the 29 Ig tested, 6 had detectable binding activity for the native gp 120 molecule.

FIG. 9B presents results from one peptide inhibition experiment that was carried out using HEA, a VH3 IgM which avidly binds to gp120. Absorbances for IgM binding were determined for peptide-treated IgM, and expressed as percent absorbance of untreated IgM (% Binding). As with serum IgM, most of the competitor peptides failed to inhibit binding of HEA to native gp120. However, 6 peptides strongly inhibited the binding to gp120 as shown in the figure. Of these 6 inhibitory peptides, two pairs (#1959/1960 and #1988/1989) were overlapping. Only one peptide (#1589) from the other strains of HIV-1 inhibited the binding of HEA to gp120 as shown in FIG. 11. Peptide #1589 is a C4 peptide from HIV-1 IIIB gp120 which overlaps HIV-1 MN peptide #2007.

It was important to resolve whether this pattern of peptide reactivity was unique to HEA, or whether it was shared by other endogenous gp120-reactive antibodies. To evaluate this point, a parallel set of experiments was performed with the other human monoclonal antibodies. Again, only a small number of peptides had competitive binding activity. Some of the inhibitory peptides were common to all IgM while the activity of other peptides was restricted to subsets of these antibodies.

Example 22 demonstrates the method used to identify the minimal gp 120 amino acid sequence that exhibited super-antigen activity.

EXAMPLE 22

Determination of the Minimal Consensus Sequence of the gp120 Ig Superantigen

Samples of serum IgM paraproteins were obtained from patients with Waldenstrom's macroglobulinemia and multiple myeloma (gifts of Drs. Thomas Kipps, James Berenson, and Mary Territo). All patients were HIV seronegative. Ig samples were aliquotted and stored at −20° C. Many of the paraproteins were used as unpurified serum since the purity relative to total serum Ig, was 50–90%.

The monoclonal IgM HEA and VIN, and the human polyclonal IgM (Sigma), were purified by ion exchange chromatography or by gel filtration. Antibody concentrations were determined by an isotype-specific ELISA as described by Sasso et al., in *J. Immunol.* 142:2778 (1989). Antibodies were used in the peptide competition assay at the following final concentrations: 1 µg/ml of polyclonal serum IgM, 1 µg/ml of HEA, 3/µg/ml of VIN, 0.4 µg/ml of RSJ, and 3 µg/ml of VNG. These doses were found to be within the linear range for the direct binding of IgM to gp120.

As summarized in FIG. 12, each antibody recognized a distinct subset of gp 120 peptides. Some of the peptides had binding activity for most of the immunoglobulins (e.g., #1919, 1959/1960, 1988, and 2007), while other peptides specificity for a subset of the antibodies (e.g., #1934 and 2008). However, only two peptide epitopes, #1919 and #1959/1960, bound to all of the monoclonal antibodies as well as to polyclonal serum IgM. Therefore, these peptides contain the optimal peptide epitope for the Ig-SAg binding site. Comparison of the sequences of the overlapping peptides #1959 and #1960 suggested a 10 amino acid segment, KGSCKNVSTV (SEQ ID NO:32), was responsible for Ig binding (FIG. 11). A strikingly similar amino acid motif was also present in peptide #1919 (KGIRRNYQHW) (SEQ ID NO:33). If the 10 amino acid sequence in #1919 is compared with the #1959/1960 motif, there are 3 amino acids which are identical, and 8 out of 10 residues which possess similar charge or hydrophobicity.

Since each IgM sample bound to a subset of gp120 peptides in addition to #1919 and #1959/1960, this suggested these additional peptides were homologous to the optimal gp120 Ig-SAg sequence. To deduce a consensus gp120 epitope which could bind to HEA, we first determined the 10-mer amino acid sequence from each active peptide which most likely accounted for its antibody binding. This was determined this by comparing the activities of overlapping peptides from the C2, C3, and C4 regions as shown in FIG. 11. This comparison revealed 3 decamer sequences that exhibited remarkable homology as evidenced by the entries in Table 8. The consensus sequence, presented in the table was derived for the gp120 motif which bound HEA. To validate this consensus, we analyzed peptides that lacked binding activity. Among the 24 non-binding peptides, most included sequences with >5 mismatches. Examples of non-binding peptides with appreciable homology to the consensus sequence are shown in Table 8. Each of these has ≧2 significant mismatches. In contrast, sequences from binding peptides displayed a maximum of 1 conservative mismatch.

TABLE 8

Consensus sequence of peptides which bind to HEA

| Peptide | Mismatches | HEA Binding | 1 | 2 | 3 | 4 | 5 | 6 | 7 | 8 | 9 | 10 | |
|---|---|---|---|---|---|---|---|---|---|---|---|---|---|
| Consensus | | | K | n | I | x | p | a | x | Q | x | V | n = nonpolar (n.p.) |
| | | | | | | | | | | | | | p = polar |
| | | | | | | S (SEQ ID NO: 43) | | | | | | | a = aliphatic n.p. |
| | | | | | | | | | | | | | x = any amino acid |
| 1959/1960 | 1 | + | K | G | S | C | K | N | V | S | T | V | (SEQ ID NO: 32) |
| 1919 | 1 | + | K | G | I | R | R | N | Y | Q | H | W | (SEQ ID NO: 33) |
| 2007 | 0 | + | K | Q | I | I | N | M | W | Q | E | V | (SEQ ID NO: 34) |
| 1589 | 0 | + | K | Q | I | I | N | M | W | Q | K | V | (SEQ ID NO: 35) |
| 1988/1989 | 1 | + | K | W | N | D | T | L | R | Q | I | V | (SEQ ID NO: 36) |
| 703 | 2 | − | K | Q | I | I | N | R | W | Q | V | | (SEQ ID NO: 37) |
| 1987 | 3 | − | K | N | I | I | G | T | R | Q | A | H | (SEQ ID NO: 38) |
| 743 | 3 | − | T | G | P | C | T | N | V | S | T | V | (SEQ ID NO: 39) |
| 1990 | 4 | − | K | N | I | I | G | T | I | R | Q | A | (SEQ ID NO: 40) |
| 2008 | 5 | − | K | A | M | Y | A | P | P | I | E | G | (SEQ ID NO: 41) |
| 1923 | 5 | − | K | E | A | T | T | T | L | F | C | A | (SEQ ID NO: 42) |

We further investigated the mechanism by which VH3 IgM inhibited HIV infection of T cell targets. According to the simplest model, VH3 IgM and CD4 bind to, and compete for, stearically related sites on the gp120 ligand. However, the results described below favor a different model wherein the complex between VH3 IgM and gp120 is sequestered by non-T cells.

Example 23 clarifies the mechanism by which VH3 IgM inhibits HIV infection of PBL in vitro. Our results unexpectedly support a model wherein VH3 IgM redirects HIV into non-T-cells by a mechanism that we term "cellular sequestration."

EXAMPLE 23

VH3 IgM Does Not Directly Compete CD4 Binding of gp120

Two different approaches were used to investigate the mechanism by which VH3 IgM inhibits HIV infection of target T cells. An ELISA protocol was employed in the first case. In a second approach, a flow cytometric analysis was performed. The procedures employed in this latter analysis have been described by Berberian et al., in *Science* 261:1588 (1993), the disclosure of which is hereby incorporated by reference.

In the first assay, the wells of an ELISA plate were coated with gp120 as described under Example 4. Biotinylated soluble CD4 was separately preincubated with varying concentrations of VH3 IgM. These mixtures were then added to the gp 120-coated wells, and the binding of gp 120 to CD4 was measured using avidin-linked peroxidase according to standard procedures that are well known to those having ordinary skill in the art. The results presented in FIG. 13 argued against a mechanism involving binding site competition.

In a second approach, we separately used CEM T cells and a heterogeneous T cell population present in whole blood as targets for gp120 binding. Samples of gp120 were first preincubated with different amounts of VH3 IgM. Subsequently, the mixtures of VH3 IgM and gp120 were combined with each of the two cell populations. After double-staining for gp120 and T cell markers, the cell samples were analyzed by flow cytometry. As shown in FIG. 13, we unexpectedly found that VH3 IgM did not inhibit the binding of gp120 to CEM cells, but did inhibit the binding of gp120 to T cells that were members of a heterogeneous population of cells.

This difference led us to investigate the mechanism by which the interaction between gp120 and T cells could be inhibited by VH3 IgM only in the presence of a mixed population of non-T cells. We first isolated PBL from whole blood and then depleted the sample of T cells. Next, we tested the resulting collection of non-T cells for activity that inhibited gp120 binding to CEM targets in the presence of VH3 IgM. The number of gp120 bound CEM cells decreased sharply with the addition of increasing numbers of non-T target cells.

Instead of neutralizing the interaction between CD4 and gp120, VH3 IgM inhibited gp120 binding to T cells according to a different mechanism. In particular, we discovered that the complex between gp120 and VH3 IgM was sequestered into cells bearing Fc receptors. Thus, VH3 IgM effectively redirected the gp120 ligand, and presumably the HIV virion, away from T cell targets and into FcR+ cells, including B cells and NK cells. We refer to this process as "cellular sequestration" of the virus.

Given our findings to this point, we went on to investigate whether other superantigens could interfere with the association between gp120 and VH3 IgM. In particular, we tested peptides or proteins that either did or did not contain the homologous decamer sequences that we demonstrated had superantigen activity. The positive controls in this procedure were the 1919 peptide and thyroglobulin. Negative controls, that did not contain the conserved decamer sequence, were the 1925 peptide and actin.

Example 24 illustrates a competition binding assay. The results of this assay confirmed that peptides or proteins harboring the conserved decamer sequence could inhibit VH3 binding to gp120.

EXAMPLE 24

Inhibition of the gp120 Binding by VH3 IgM with Non-HIV Superantigens

The wells of an ELISA plate were coated with gp120 protein according to standard procedures. A fixed concentration of VH3 IgM was preincubated with each of four candidate competitors at specified concentrations. The candidate competitors were Actin, peptide 1925, thyroglobulin and peptide 1919. The mixtures of gp120 and VH3 IgM were then added to the gp120 coated ELISA wells. After removing unbound VH3 IgM by a standard washing procedure, VH3 IgM immobilized to gp120 was quantitated using enzyme-linked anti human IgM as a reporter.

The results presented in FIG. 14 clearly indicated that neither actin nor the 1925 peptide inhibited the association between cp120 and VH3 IgM. Conversely, the 1919 peptide and thyroglobulin both inhibited gp120 binding to VH3 IgM.

Given our findings, we believe that proteins or peptides that harbor the conserved decamer sequence can be adapted for use as therapeutic agents that interfere with entry of HIV into T cells.

We also believe that agents such as the 1919 peptide or thyroglobulin that have superantigen binding activity can be administered as immunogens to stimulate increased levels of VH3 Ig. Enhanced VH3 Ig levels would not be expected to eliminate HIV from an infected person, but would instead be effective in redirecting the virus away from T cells and into other cell types where infection would be less detrimental to the patient's health.

The experimental results presented above have shown that HIV-1 gp120 is a novel virus encoded Ig-SAg. These results also represent the first characterization of a minimal peptide sequence recognized by an Ig-SAg binding interaction. A panel of five antibodies from HIV seronegative individuals (polyclonal IgM plus four independent monoclonal IgMs) shared specificity for a peptide from the C1 region of gp120 (#1919) and for two overlapping peptides from the C2 region (#1959/1960). Each of these shared peptides abolished the binding of IgM to gp120, indicating that a linear sequence common to all 3 peptides accounted for the Ig-SAg binding of gp120. Comparison of these peptides revealed a homologous core of 10 amino acids. Within this core sequence, 3 residues were identical and 8 out of 10 amino acids had similar charges or hydrophobicities. The findings summarized above support the hypothesis that binding of gp 120 to Ig involves a conserved site(s) on gp120 as well as a conserved region within a family of VH3 gene products.

Interestingly, the monoclonal IgM VNG also bound to a peptide from the surface-exposed third hypervariable region (V3) of gp120 (peptide #1985). Peptide #1985 does not inhibit the binding of endogenous polyclonal serum IgM to gp120, so VNG IgM probably represents only a minor component of the normal Ig repertoire. The V3 loop of gp120 is critical for HIV infection, and as such, is an immunodominant epitope during the immune response to HIV, as described by Javaherian et al., in Proc. Natl. Acad. Sci. USA. 86:6768 (1989). Whether the levels of VNG Ig vary in the normal population or during the course of HIV infection remains to be determined. Nevertheless, it is interesting to speculate that the binding of subpopulations of endogenous VH3 Ig (e.g., VNG) to exposed gp120 epitopes (i.e., C4, C5-gp41, or V3 loop), may affect the life cycle or tropism of the virus.

General immunoregulatory processes affecting immunoglobulin secretion

Immunoglobulin secretion by B-lymphocytes is regulated by a variety of cell types through direct cell-cell interaction (complementary membrane protein binding) and secreted trophic factors (eg., cytokines). Thus, any of a number of pharmacologic or immune manipulations of natural anti-gp120 B-cells are within the scope of the present invention. Examples of such manipulations are use of immunosuppressive agents such as kinase inhibitors or cyclosporine that interferes with intracellular signalling or lymphocyte cell physiology; anti-receptor antibodies against membrane proteins for T-B interaction (eg., B7, CD28, CD72, CD5); anti-cytokine antibodies against IL-6 or IL-2; and use of immunoglobulin-suppressive cytokines (eg., TGF-beta).

Other pharmacologic antagonists, including but not limited to active subcomponents or other functional homologues of HIV gp120 or VH3 gene products that interfere with the association of VH3 immunoglobulins and HIV gp120 are also part of the present invention.

In addition, immunization proceduresthat generate neutralizing antibodies against the sites on gp 120 or immunoglobulin involved in the gp120-immunoglobulin association are also meant to be within the scope of the invention. For example, a recombinant vaccinia virus can be designed to express an active peptide subcomponent of HIV gp120 or VH3 immunoglobulin. Immunization of individuals with this recombinant virus could result in neutralizing antibodies of sufficient titer and persistence to protect the individual from future HIV infection.

Human immunoglobulins are remarkably conserved at the coding level, and it is likely that this conservation is at least in part due to positive selection by complementary superantigens. Thus, we anticipate robust efforts to identify physiologic and pathophysiologic settings involving superantigen-immunoglobulin interactions. Part of the present invention is a two-step strategy for identifying these settings.

First, a prospective setting is evaluated by testing for the relative abundance of immunoglobulins or B-lymphocytes bearing different variable region gene segments. These may be identified by anti-idiotypic antibodies; in the latter case, nucleic acid analytic methods may also be used (eg., V family-selective PCR and gene-specific oligonucleotide hybridization). The positive criterion in this test is over- or under-representation of one or a small subset of variable region gene-segments. Second, representative immunoglobulins bearing these variable region gene-segments are isolated, and used to test for association with candidate superantigens. Association may be evaluated by typical analytic methods, including ELISA, flow cytometry, etc. It also should be emphasized that these representative immunoglobulins can also be employed using immunoaffinity-based biochemical methods to isolate undefined superantigens.

This invention has been described with reference to a number of specific examples and embodiments thereof. However, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of determining the HIV-1 disease state of a patient infected with HIV-1, comprising:
   obtaining a biological sample from said patient, said sample containing antibodies;
   determining the level of VH3-containing antibodies having gp120 binding activity in said sample; and
   comparing the determined level of said antibodies with a predetermined level of said antibodies in a biological sample from an asymptomatic HIV-1 infected patient, wherein a lower level in said biological sample from said patient relative to said predetermined level is indicative of a disease state more advanced than said asymptomatic HIV-1 infected patient.

2. The method of claim 1, wherein said sample comprises serum.

3. The method of claim 1, wherein said VH3-containing antibodies are determined by binding to paraprotein B6.

* * * * *